(12) United States Patent
Fukuzawa et al.

(10) Patent No.: US 8,114,108 B2
(45) Date of Patent: Feb. 14, 2012

(54) LANCING APPARATUS

(75) Inventors: Masahiro Fukuzawa, Kyoto (JP); Yoshiharu Uehata, Kyoto (JP)

(73) Assignee: Arkray, Inc. (JP)

( * ) Notice: Subject to any disclaimer, the term of this patent is extended or adjusted under 35 U.S.C. 154(b) by 997 days.

(21) Appl. No.: 10/552,841

(22) PCT Filed: Apr. 12, 2004

(86) PCT No.: PCT/JP2004/005223
§ 371 (c)(1), (2), (4) Date: Oct. 11, 2005

(87) PCT Pub. No.: WO2004/091401
PCT Pub. Date: Oct. 28, 2004

(65) Prior Publication Data
US 2006/0200181 A1  Sep. 7, 2006

(30) Foreign Application Priority Data

Apr. 11, 2003  (JP) .................................. 2003-107869
Nov. 21, 2003  (JP) .................................. 2003-392743

(51) Int. Cl.
*A61B 17/32* (2006.01)
(52) U.S. Cl. ..................................................... 606/182
(58) Field of Classification Search ................ 600/573, 600/578, 583; 606/181–183
See application file for complete search history.

(56) References Cited

U.S. PATENT DOCUMENTS

| 4,643,189 | A | * | 2/1987 | Mintz | 606/182 |
| 4,924,879 | A | * | 5/1990 | O'Brien | 600/583 |
| 5,196,025 | A | * | 3/1993 | Ranalletta et al. | 606/182 |
| 5,318,583 | A | * | 6/1994 | Rabenau et al. | 606/182 |
| 5,318,584 | A | * | 6/1994 | Lange et al. | 606/182 |
| 6,409,740 | B1 |   | 6/2002 | Kuhr et al. | |
| 6,607,543 | B2 | * | 8/2003 | Purcell et al. | 606/181 |
| 6,929,649 | B2 | * | 8/2005 | Pugh | 606/182 |
| 7,144,404 | B2 | * | 12/2006 | Whitson et al. | 606/181 |
| 7,470,238 | B2 | * | 12/2008 | Sakata et al. | 600/583 |
| 2003/0028126 | A1 | * | 2/2003 | List | 600/583 |
| 2003/0225429 | A1 | * | 12/2003 | Garthe et al. | 606/182 |

FOREIGN PATENT DOCUMENTS

| EP | 1 230 895 | 8/2002 |
| JP | 64-42010 | 3/1989 |
| JP | 2688800 | 8/1997 |
| JP | 2702374 | 10/1997 |
| JP | 2002-369815 | 12/2002 |

* cited by examiner

*Primary Examiner* — Ryan Severson
*Assistant Examiner* — David Eastwood
(74) *Attorney, Agent, or Firm* — Studebaker & Brackett PC; Donald R. Studebaker

(57) ABSTRACT

A lancing apparatus that moves a lancing element in a lancing direction from a wait position to a lancing position thereby lancing an intended portion with the lancing element. The lancing apparatus has a first member which moves reciprocally in the lancing direction and in the retreating direction. A second member moves with the lancing element and performs reciprocal movement in the lancing and retreating directions in accordance with the movement of the first member.

28 Claims, 29 Drawing Sheets

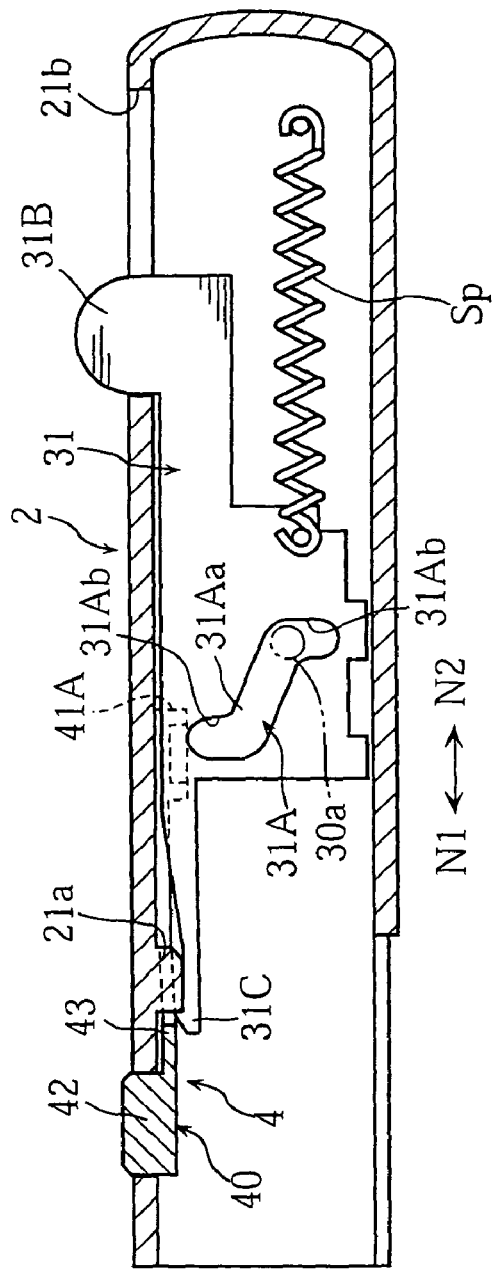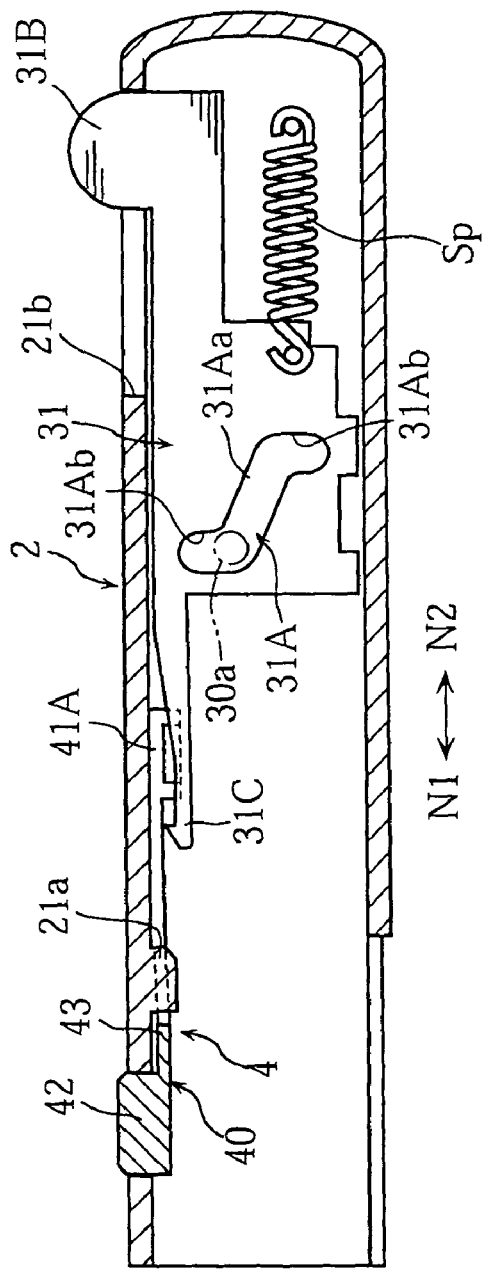

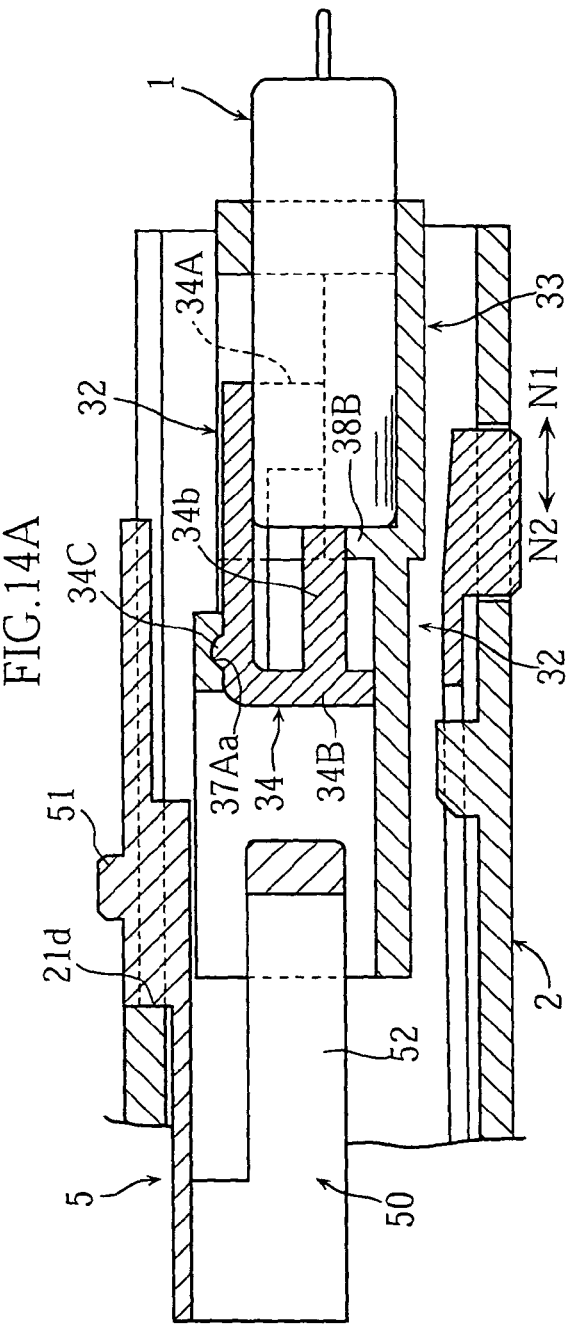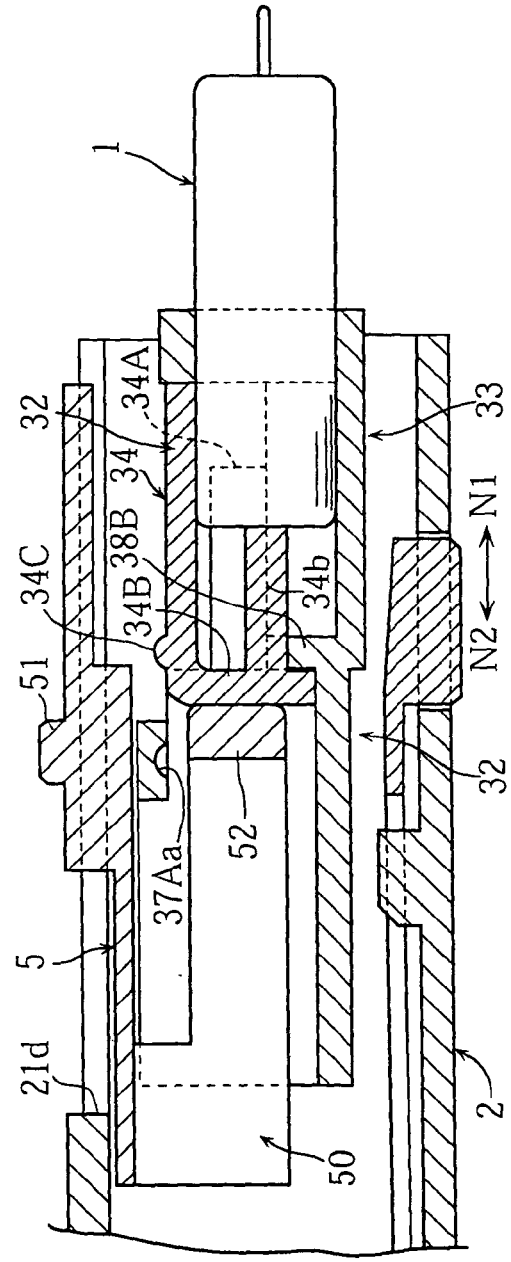

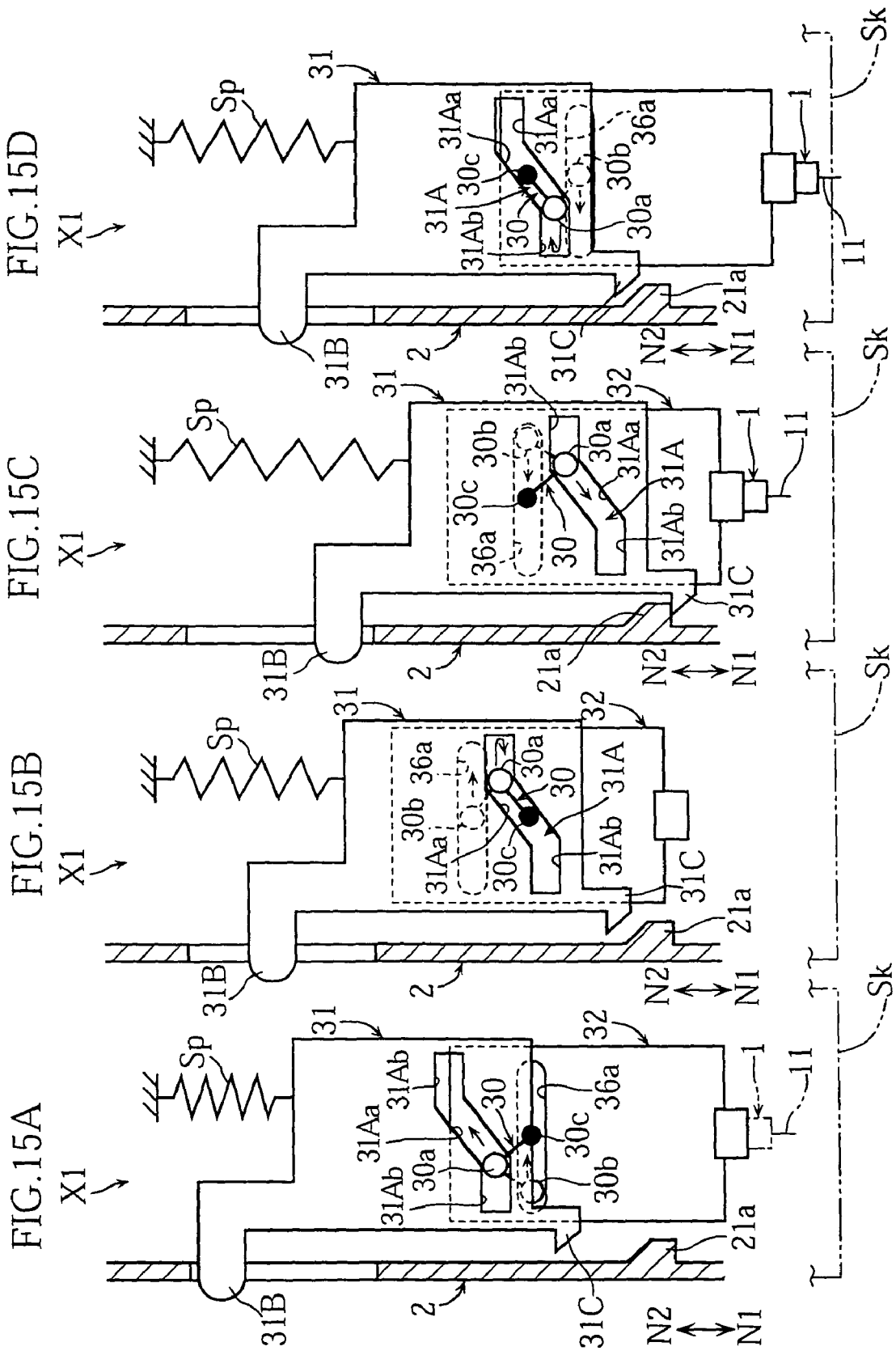

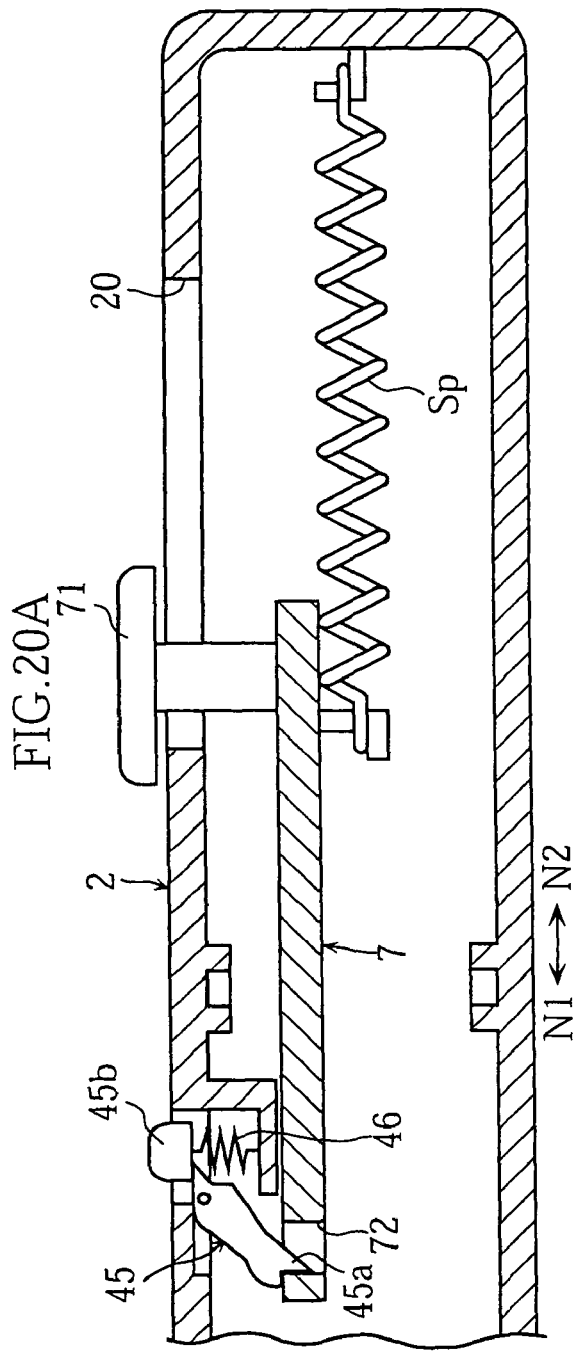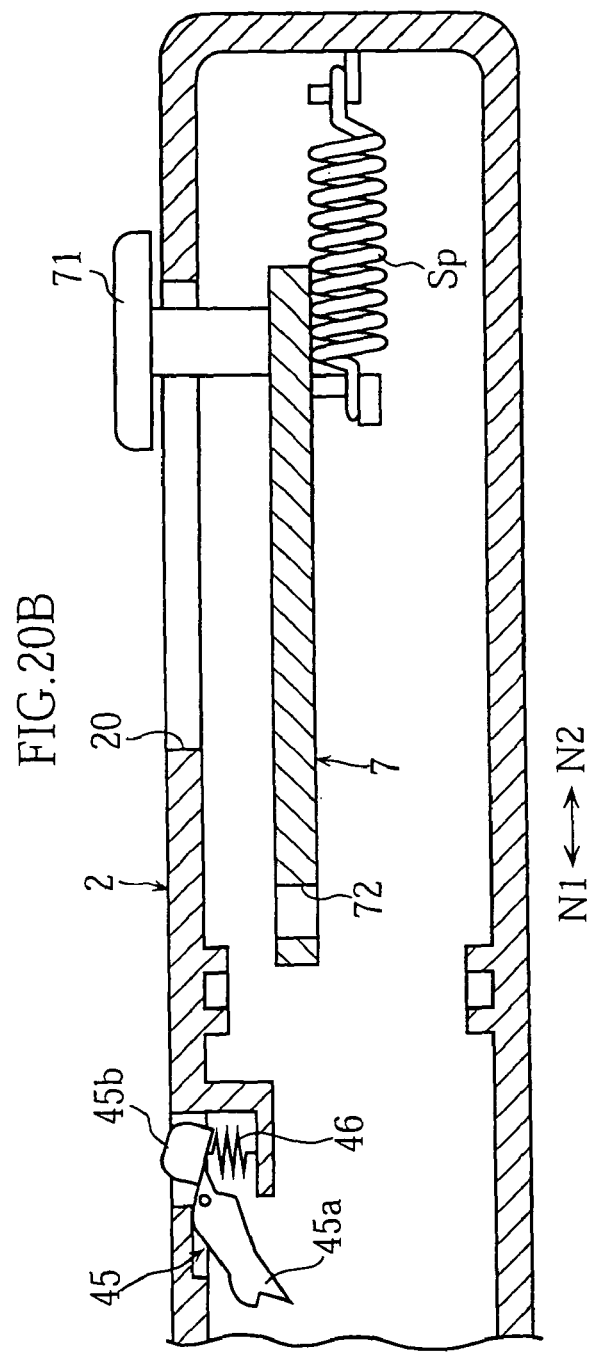

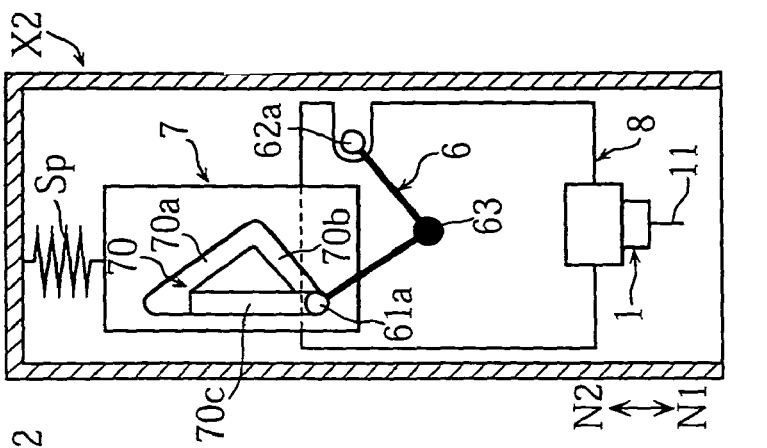
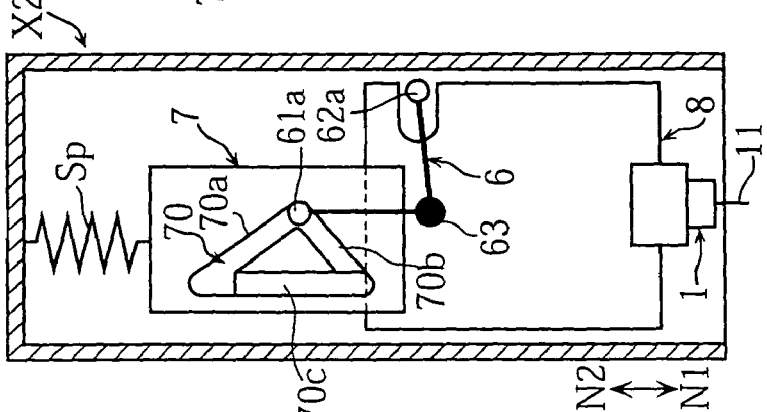
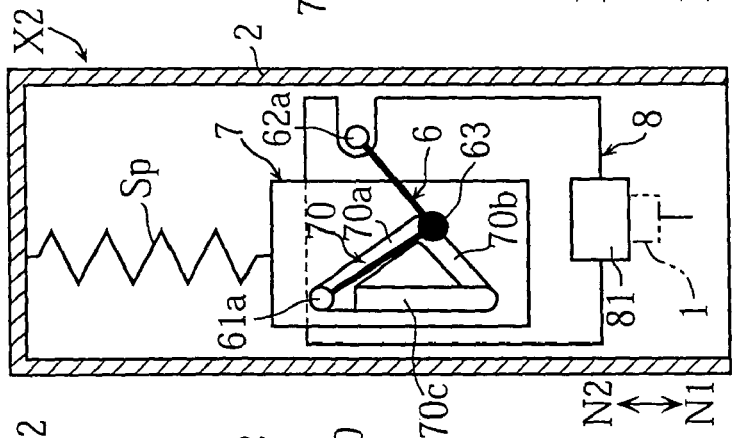
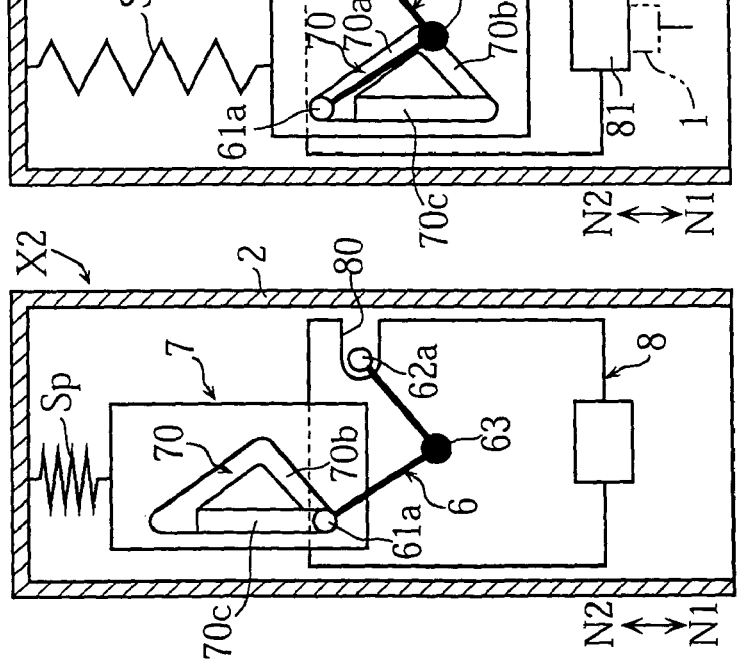

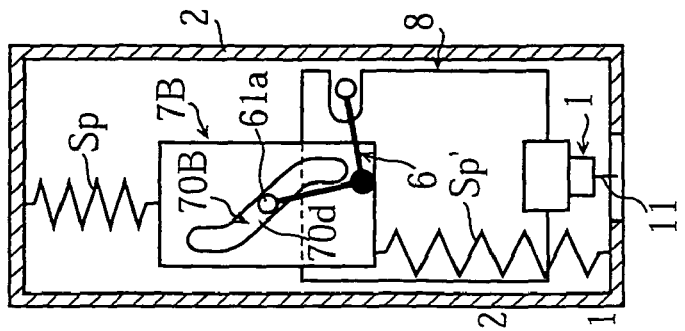
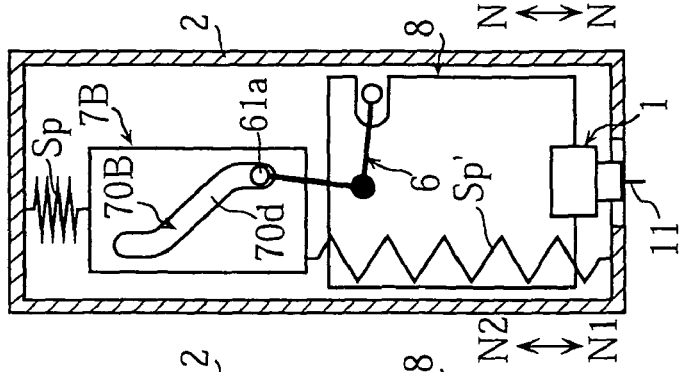
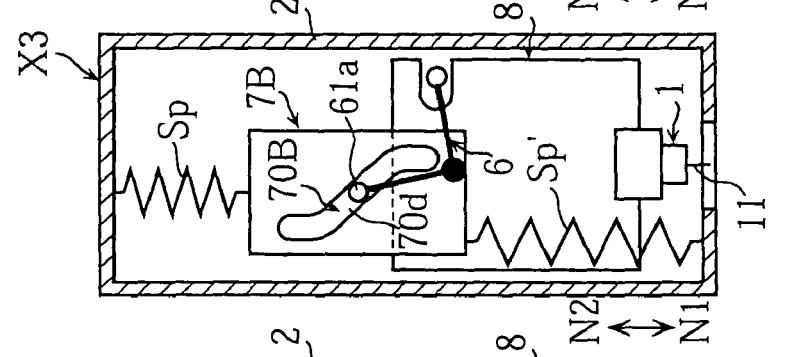
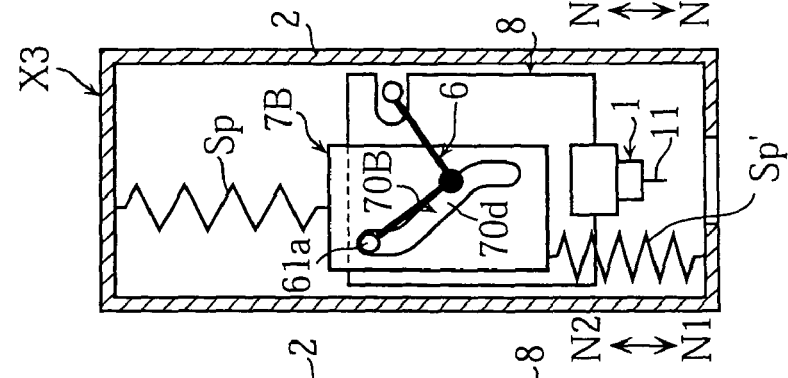
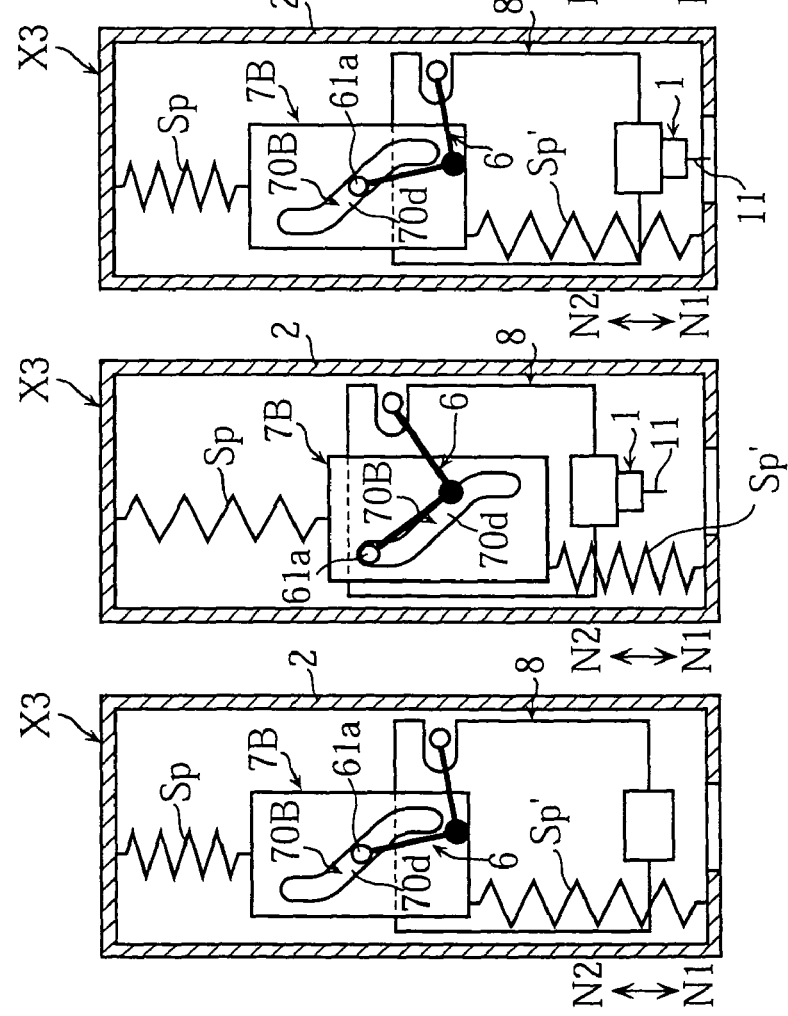

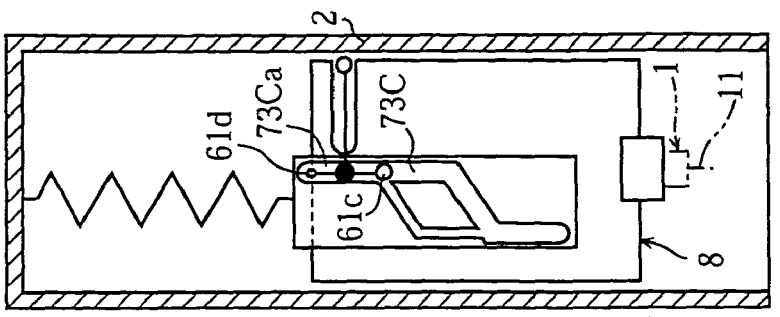
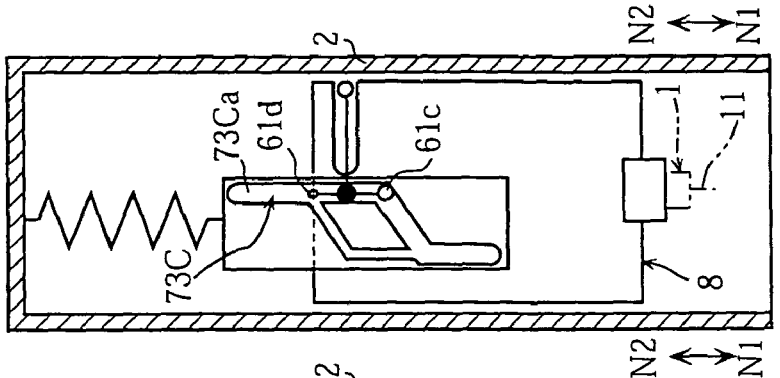
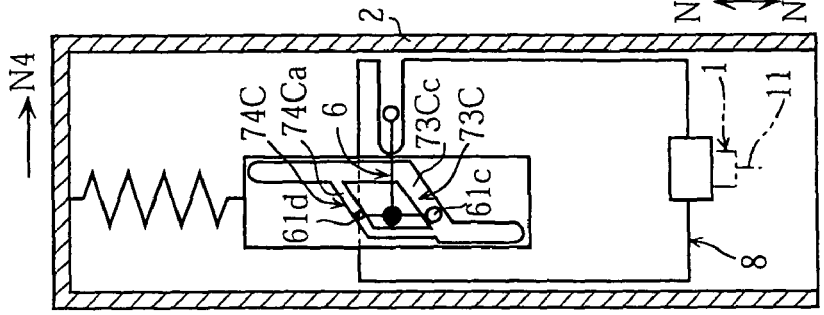
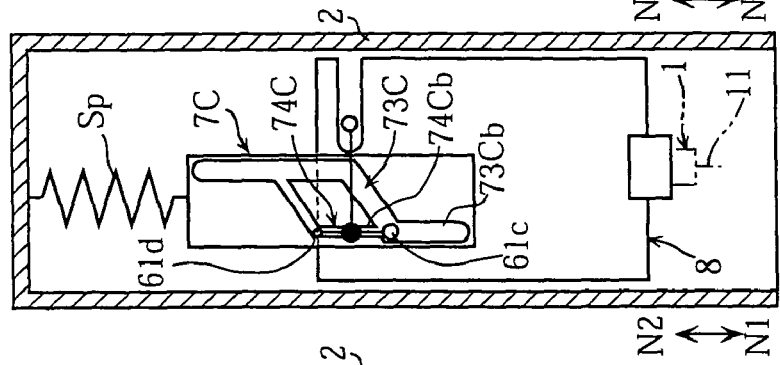
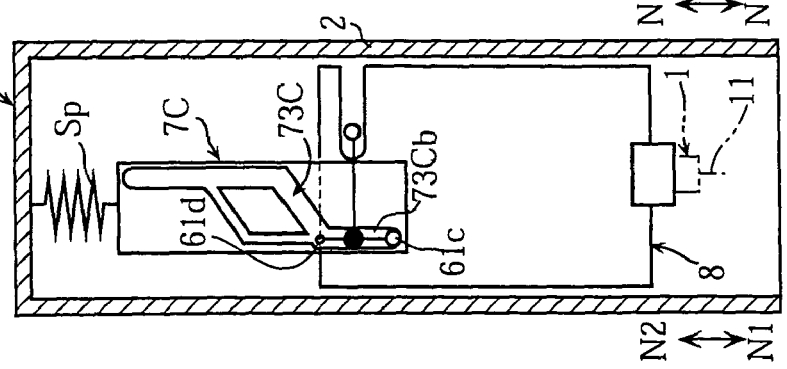

LANCING APPARATUS

TECHNICAL FIELD

The present invention relates to a lancing apparatus used to extract blood or tissue from skin, for example.

BACKGROUND ART

FIGS. 33A-33C show an example of lancing apparatus. The lancing apparatus 90 shown in the figures includes a lancet 902 which is moved along with a lancet holder 901 by the resilient force of a coil spring 900 to lance skin. As shown in FIG. 33A, in the lancing apparatus 90, the coil spring 900 can be kept in the state for storing the resilient force by latching an engagement claw 903 of the lancet holder 901 to a stepped portion 905 of a housing 904. As shown in FIG. 33B, the latched state can be released by pushing an operation cap 906 to bring an operative portion 907 of the operation cap 906 into contact with the engagement claw 903 and disengaging the engagement claw 903. As shown in FIG. 33C, when the latched state is released, the resilient force of the coil spring 900 acts on the lancet holder 901 to move the lancet 902, along with the lancet holder 901, in a lancing direction N1. As a result, the lancet 902 sticks in skin.

Another example of lancing apparatus utilizes a cam mechanism for lancing skin with the lancet (See JP-U 64-42010 and JP Patent No. 2702374, for example).

FIGS. 34A-34C show the lancing apparatus disclosed in JP-U 64-42010. In the lancing apparatus, the rotational movement of a cam 910 is converted into reciprocal movement of a lancet supporter 911, and the lancet 92 is moved along with the lancet supporter 911 to lance the skin. Shown in FIG. 34A is a lance wait state of this lancing apparatus 91, in which the cam 910 is fixed, with the coil spring 913 storing the resilient force. From this state, by operating a rotation lever 914, the cam 910 is released from the fixed state, as shown in FIGS. 34B and 34C. As a result, the cam 910 rotates around a shaft 915. The cam 910 is formed with a V-shaped cam groove 916, with which an engagement pin 917 integrally formed on the lancet supporter 911 engages. Therefore, when the cam 910 rotates, the engagement pin 917 moves along the cam groove 916. As a result, the lancet supporter 911 moves reciprocally in the lancing direction N1 and the retreating direction N2 while being guided by a slide hole 918, whereby the lancet 912, along with the lancet supporter 911, moves reciprocally in the lancing and the retreating directions N1 and N2.

The lancing apparatus 91 further includes a mark member 919 for preventing the lancet 912 from unintentionally projecting in a non-lancing period to enhance the safety and realizing a proper lancing depth. The mark member 919 includes a slide member 919A, and a mark plate 919B which moves along with the slide member 919A. The side member 919A and the mark plate 919B are biased toward the lancing direction N1 and can be moved in the retreating direction N2 by pressing the lancing apparatus 91, with the mark plate 919B held in contact with the skin.

As shown in FIG. 35, the lancing apparatus disclosed in JP Patent No. 2702374 includes a housing 920 accommodating a transmission member 921 and a lancet holder 922. The lancet holder 922 can be moved in the lancing and the retreating directions N1 and N2 due to the rotation of the transmission member 921. The transmission member 921 is rotatable in the circumferential direction in close contact with the inner surface of the lancet holder 922 and supported by the housing 920 via a coil spring 923. The transmission member 921 is provided with a drive pin 925 for engagement with a drive cam 924 of the lancet holder 922. As shown in FIG. 36, the drive cam 924 includes a first segment 924a along which the drive pin 925 moves in moving the lancet holder 922 (See FIG. 35) in the lancing direction N1, a second segment 924b along which the dive pin 925 moves in moving the lancet holder 922 (See FIG. 35) in the retreating direction N2, and a third segment 924c along which the drive pin 925 moves in twisting the coil spring 923 (See FIG. 35) for storing the resilient force.

As shown in FIG. 35, the transmission member 921 is also connected to a sealing ring 926 provided at the front end of the housing 920. By rotating the sealing ring 926, the drive pin 925 of the transmission member 921 moves in the circumferential direction to twist the coil spring 923. The transmission member 921 can be fixed by non-illustrated fixing means, with the coil spring 923 twisted and storing the resilient force. When the operation button 927 is pressed, the transmission member 921 can be released from the fixed state.

In the lancing apparatus 90 shown in FIGS. 33A-33C, after the resilient force of the coil spring 900 is transmitted to the lancet holder 901, the lancet holder 901 moves independently from the coil spring 900. Therefore, to move the lancet holder 901 smoothly, a relatively large gap is defined between the lancet holder 901 and the housing 904 in the lancing apparatus 90. Therefore, in the lancing apparatus 90, when the lancet holder 901 is released from the latched state and moved in the lancing direction N1, the lancet holder 901 and hence the lancet 902 are liable to tremble, so that the lancet 902 is liable to shake in the lancing operation. Such shake gives the user unnecessary pain.

Further, in the lancing apparatus 90, the movement of the lancet holder 901 in the lancing direction N1 is stopped when the lancet holder 901 engages the stepped portion 908 of the housing 904. Therefore, in the lancing, the impact caused by the engagement of the lancet holder 901 with the stepped portion 908 is transmitted to the skin. Such impact not only causes pain or discomfort but also transmits vibration to the lancet 902, which further increases pain in the lancing. In addition, the impact noise upon the engagement increases the feeling of the pain, and the impact noise combined with the pain due to lancing gives greater discomfort.

In the lancing apparatus 91 shown in FIGS. 34A-34C, the movement of the lancet supporter 911 is guided by the slide hole 918, so that shake of the lancet 912 is unlikely to occur. Since the lancet supporter 911 is reciprocated by the cam mechanism, the transmission of large impact to the skin and the generation of large impact sound do not occur. However, since the lancing apparatus 91 is provided with the mark member 919 for enhancing the safety in the non-lancing period, the structure of the apparatus is complicated and disadvantageous in terms of the manufacturing cost. Further, the mark member 919 is so designed that the adjustment of the pressing force exerted to the mark member for controlling the lancing depth is performed by the user's operation. Therefore, when the exerted pressing force is too small, the lancing depth becomes too small to obtain sufficient blood. Conversely, when the exerted pressing force is too large, the lancing depth becomes too large, which may cause unnecessary pain. In this way, the adjustment of the lancing depth is difficult, and the lancing apparatus 91 is inconvenient.

In the lancing apparatuses shown in FIGS. 35 and 36, the operation button 927 is pressed to move the lancet holder 922 in the lancing direction after the sealing ring 926 is rotated. Therefore, the lancing apparatus 92 is difficult to use with one hand, and hence, is inconvenient. When the coil spring 923 is twisted in use, a load is liable to be exerted onto an end of the spring 923, which shortens the lifetime of the coil spring 923.

To solve such a problem, the rigidity of the coil spring need be increased, which is disadvantageous in terms of the manufacturing cost.

DISCLOSURE OF THE INVENTION

An object of the present invention is to provide a lancing apparatus which can reduce pain and discomfort in lancing, which has good operability, and which can be manufactured at a relatively low cost.

According to the present invention, there is provided a lancing apparatus for moving a lancing element in a lancing direction from a wait position to a lancing position to lance an intended portion with the lancing element, the lancing apparatus comprising a first member which is reciprocally movable in the lancing direction and in a retreating direction which is opposite from the lancing direction, and a second member which moves along with the lancing element and performs reciprocal movement in the lancing direction and the retreating direction in accordance with the movement of the first member.

For instance, the first member is reciprocally movable between a first fixed position and a second fixed position, and the second member performs one cycle of reciprocal movement between a third fixed position and a fourth fixed position during when the first member performs one cycle of reciprocal movement between the first fixed position and the second fixed position. Preferably, in this case, the second member performs turning-back movement during when the first member moves straight between the first fixed position and the second fixed position.

For instance, the lancing element is positioned at the lancing position when the second member is positioned at the third fixed position, and the lancing element is positioned at the wait position when the second member is positioned at an intermediate region between the third fixed position and the fourth fixed position. Preferably, the lancing element moves from the wait position to the lancing position during when the first member moves in the retreating direction.

In a preferred embodiment, when the first member performs one cycle of reciprocal movement, the second member performs one cycle of reciprocal movement which is phase-shifted by 90 degrees or about 90 degrees from the first member.

Preferably, the lancing apparatus of the present invention further comprises a third member for connecting the first member and the second member to each other and converting the movement of the first member into the reciprocal movement of the second member.

For instance, the third member includes a rotation shaft whose position is fixed, a first movable portion which engages the first member and is rotatable around the rotation shaft, and a second movable portion which engages the second member and is rotatable around the rotation shaft. In this case, the first member includes a first engagement portion for allowing the rotation of the first movable portion, and the second member includes a second engagement portion for allowing the rotation of the second movable portion.

At least one of the first and the second engagement portions includes an inclined portion which is inclined with respect to a perpendicular or generally perpendicular direction extending perpendicularly to the lancing and the retreating directions. Preferably, the inclined portion has opposite ends each of which is connected to a straight portion extending in the perpendicular direction. Preferably, of the first and the second movable portions, the movable portion which engages the inclined portion moves through the inclined portion when the lancing element moves from the wait position to the lancing position and moves through the straight portion when the lancing element moves from the lancing position in the retreating direction.

However, the configurations of the first and the second engagement portions are not limitative, and other configurations may be employed as long as they can cause reciprocal movement of the second member when the first member moves.

In a preferred embodiment, the first member is fixed while being biased when the lancing element is positioned at the wait position, and the first member is moved by the biasing force when released from the fixed state.

The third member may be pivotable to convert the movement of the first member into the reciprocal movement of the second member by the pivotal movement.

In this case, the third member includes a pivot shaft, a first movable portion which engages the first member and is pivotable around the pivot shaft, and a second movable portion which engages the second member and is pivotable around the pivot shaft.

For instance, the first member includes an engagement portion for engaging the first movable portion and controlling movement of the third member in accordance with a position where the first movable portion engages. Preferably, in this case, the engagement portion includes an inclined portion for pivoting the third member to move the second member in the lancing direction. Preferably, the engagement portion includes an additional inclined portion for pivoting the third member to move the second member in the retreating direction. The engagement portion may include a straight portion for moving the first member in the lancing direction or the retreating direction without moving the second and the third members in the lancing and the retreating directions.

The lancing apparatus according of the present invention may further comprise a resilient member for moving the second member in the retreating direction after the intended portion is lanced with the lancing element.

The first movable portion may include a first and a second pins. In this case, the engagement portion includes an inclined portion with which the first pin engages in moving the second member in the lancing direction and with which the second pin engages in moving the second member in the retreating direction. The first member may include an additional engagement portion with which the second pin selectively engages when the first member moves in the retreating direction. The first pin may be made larger in diameter than the second pin. In this case, the additional engagement portion has a width which is smaller than diameters of the engagement portion and the first pin.

The first member may be movable in a crossing direction crossing the lancing and the retreating directions to pivot the third member to move the second member in the retreating direction. Specifically, the lancing apparatus of the present invention may further comprise an actuating member for moving the first member, and each of the first member and the actuating member includes an inclined surface. The first member moves in the crossing direction by moving the inclined surface of the actuating member along the inclined surface of the first member. The lancing apparatus of the present invention may further comprise a guide which moves along with the first member in the lancing direction or the retreating direction, and a resilient member for connecting the guide and the first member to each other and biasing the first member in the crossing direction crossing the lancing and the retreating directions.

BRIEF DESCRIPTION OF THE DRAWINGS

FIGS. 6A and 6B each is a sectional view for describing the internal structure of the lancing apparatus shown in FIG. 1, in which the structural elements are partially omitted.

FIGS. 14A and 14B are sectional views of the principal part for describing the lancet discharge mechanism.

FIGS. 15A-15D are schematic sectional views for describing the lancing operation of the lancing apparatus shown in FIG. 1.

FIGS. 20A and 20B are sectional views showing the principal part of the lancing apparatus shown in FIG. 17 for describing the internal structure of the apparatus, in which part of the structural elements is omitted.

FIGS. 24A-24D are schematic sectional views for describing the lancing operation of the lancing apparatus shown in FIGS. 17 and 18.

FIGS. 25A-25E are schematic sectional views showing a lancing apparatus according to a third embodiment of the present invention and the lancing operation thereof.

FIGS. 29A-29E are schematic sectional views for describing the lancing operation of the lancing apparatus shown in FIG. 26.

BEST MODE FOR CARRYING OUT THE INVENTION

The present invention will be described in detail as a first through a fifth embodiments with reference to the accompanying drawings.

First, with reference to FIGS. 1-16, a first embodiment of the present invention will be described.

Figure 1:
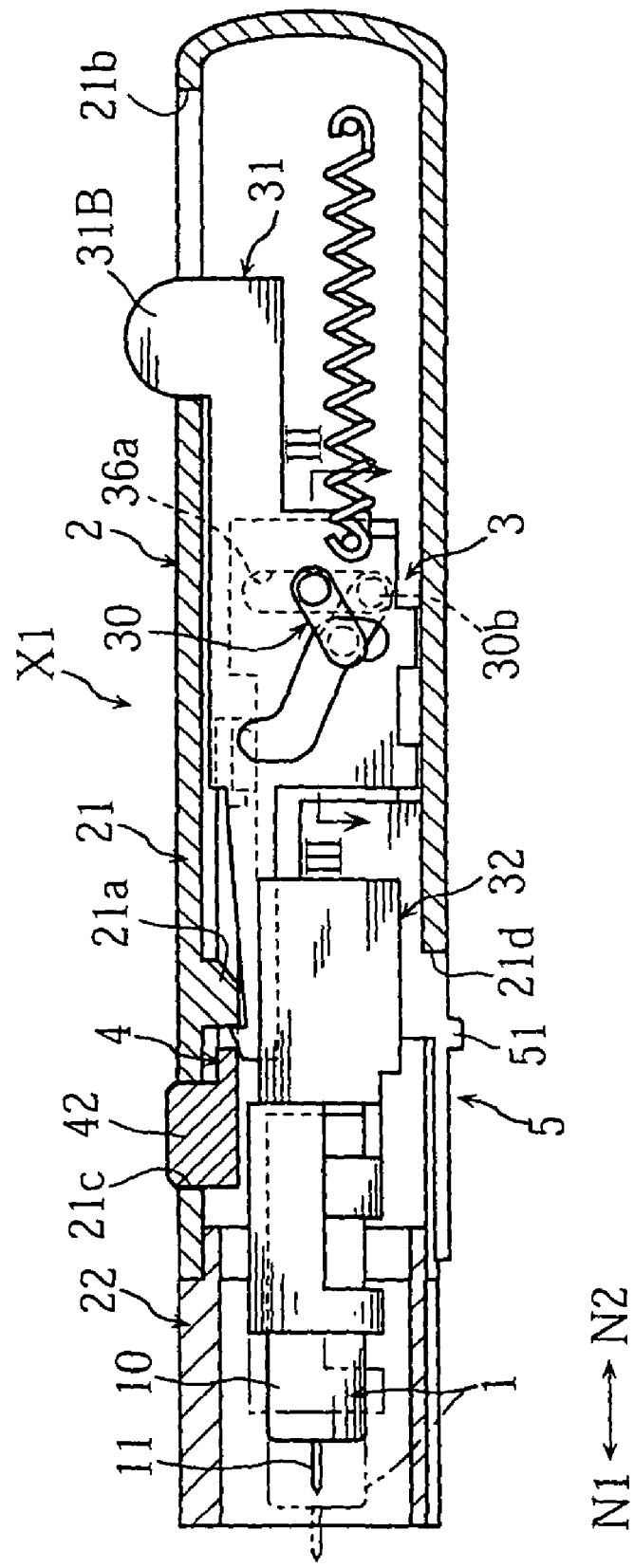
FIG. 1 is a sectional view showing a lancing apparatus according to a first embodiment of the present invention.

As shown in FIG. 1, the lancing apparatus X1 is used to lance skin and cause bleeding from the skin by moving a lancet 1 from a wait position (the position at which the lancet 1 is depicted by solid lines in the figure) to a lancing position (the position at which the lancet 1 is depicted by phantom lines in the figure). The lancing apparatus X1 includes a housing 2, a lancet moving mechanism 3, a latch release mechanism 4 and a lancet discharge mechanism 5.

The lancet 1 is an element to lance skin, as noted above, and held by a lancet holder 32 and moved by the movement of the lancet holder 32, which will be described later. The lancet 1 includes a main body 10 and a lancing needle 11 projecting from the main body and is made disposable, for example. The main body 10 is made of e.g. resin into a columnar configuration. The lancing needle 11 is made of e.g. metal and insert-molded relative to the main body 10.

The housing 2 defines a space for accommodating each element and comprises a first and a second sleeves 21 and 22.

The first sleeve 21 includes a projection 21a, and a first through a third openings 21b-21d. The projection 21a serves to engage with a movable plate 31 of the lancet moving mechanism 3. The first opening 21b serves to allow the movement of an actuating portion 31B of the movable plate 31. The second opening 21c serves to allow the movement of a press portion 42 of the latch release mechanism 4. The third opening 21d serves to allow the movement of an actuating portion 51 of the lancet discharge mechanism 5.

Figure 22:
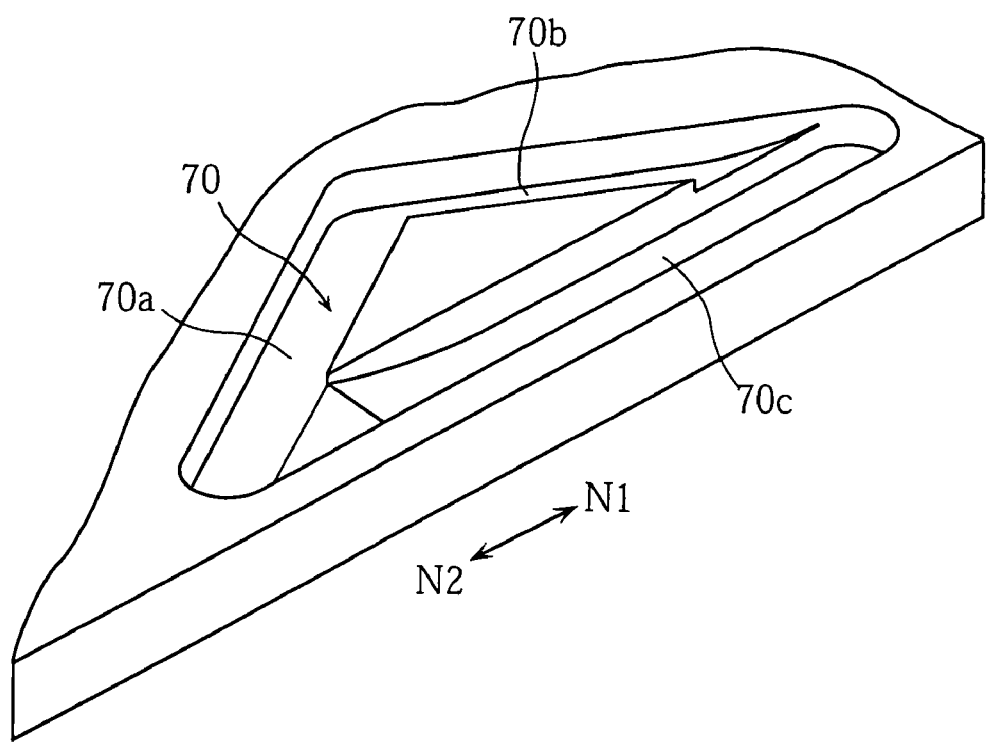
FIG. 22 is a perspective view showing the principal part of the movable plate shown in FIG. 21 as enlarged.

The second sleeve 22 is open at opposite ends thereof to allow the movement of the lancet holder 32, which will be described later. As shown in FIG. 22, the second sleeve 22 is removably attached to the front end of the first sleeve 21. With the second sleeve 22 removed from the first sleeve 21, the lancet 1 can be easily mounted to the lancet holder 32.

Figure 3:
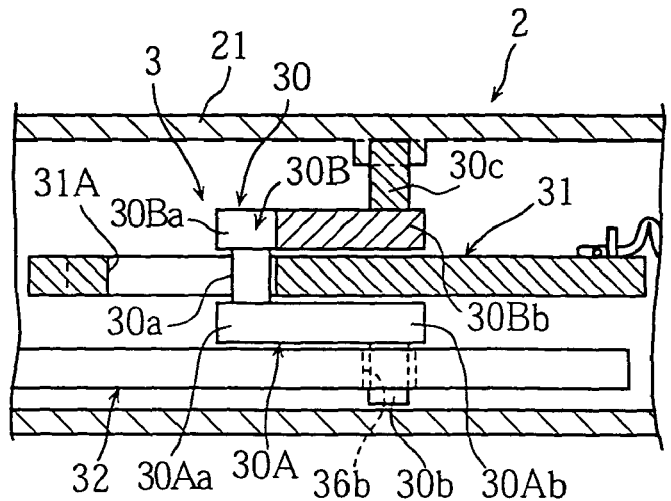
FIG. 3 is a sectional view taken along lines III-III in FIG. 1.

As shown in FIG. 3, the lancet moving mechanism 3 comprises a link member 30, the movable plate 31 and the lancet holder 32. The lancet moving mechanism 3 converts the reciprocal movement of the movable plate 31 into the reciprocal movement of the lancet holder 32 via circular motion of the link member 30.

Figure 4:
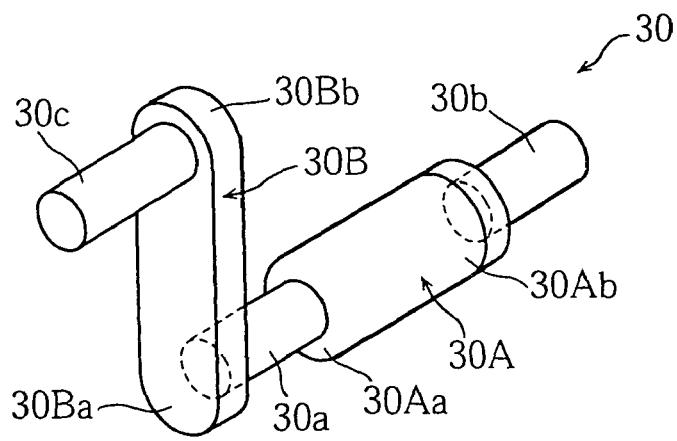
FIG. 4 is an entire perspective view of a link member.

As shown in FIGS. 3 and 4, when the movable plate 31 moves, the link member 30 moves the lancet holder 32 in accordance with the movement of the movable plate. The link member 30 includes a first movable pin 30a, a second movable pin 30b, a fixing pin 30c, a first arm 30A and a second arm 30B.

The first movable pin 30a engages the movable plate 31 and connects the first and the second arms 30A and 30B to each other. Specifically, the first movable pin 30a connects an ends 30Aa of the first arm 30A and an end 30Ba of the second arm 30B to each other so that respective other ends 30Ab and 30Bb of the first and the second arms 30A and 30B positionally deviate from each other.

The second movable pin 30b, which serves to engage the lancet holder 32, projects from the end 30Ab of the first arm 30A in the direction opposite from the first movable pin 30a.

The fixing pin 30c serves to fix the link member 30 rotatably to the housing 2 and projects from the end 30Bb of the second arm 30B in the direction opposite from the first movable pin 30a.

Figure 5:
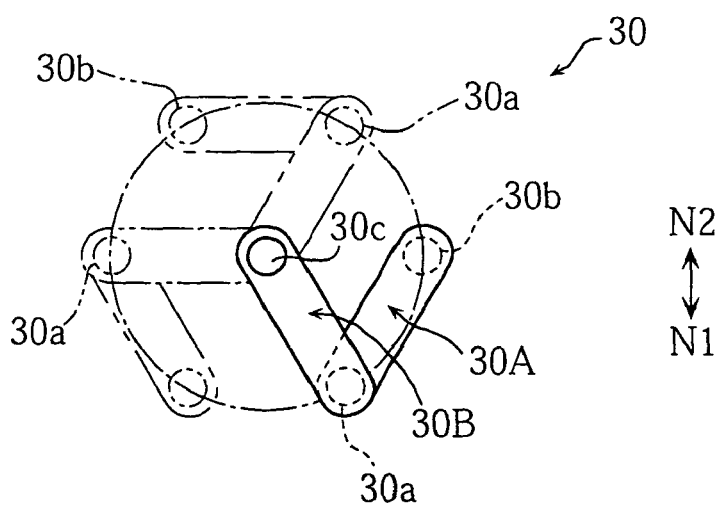
FIG. 5 is a front view for describing the operation of the link member.
Figure 16:
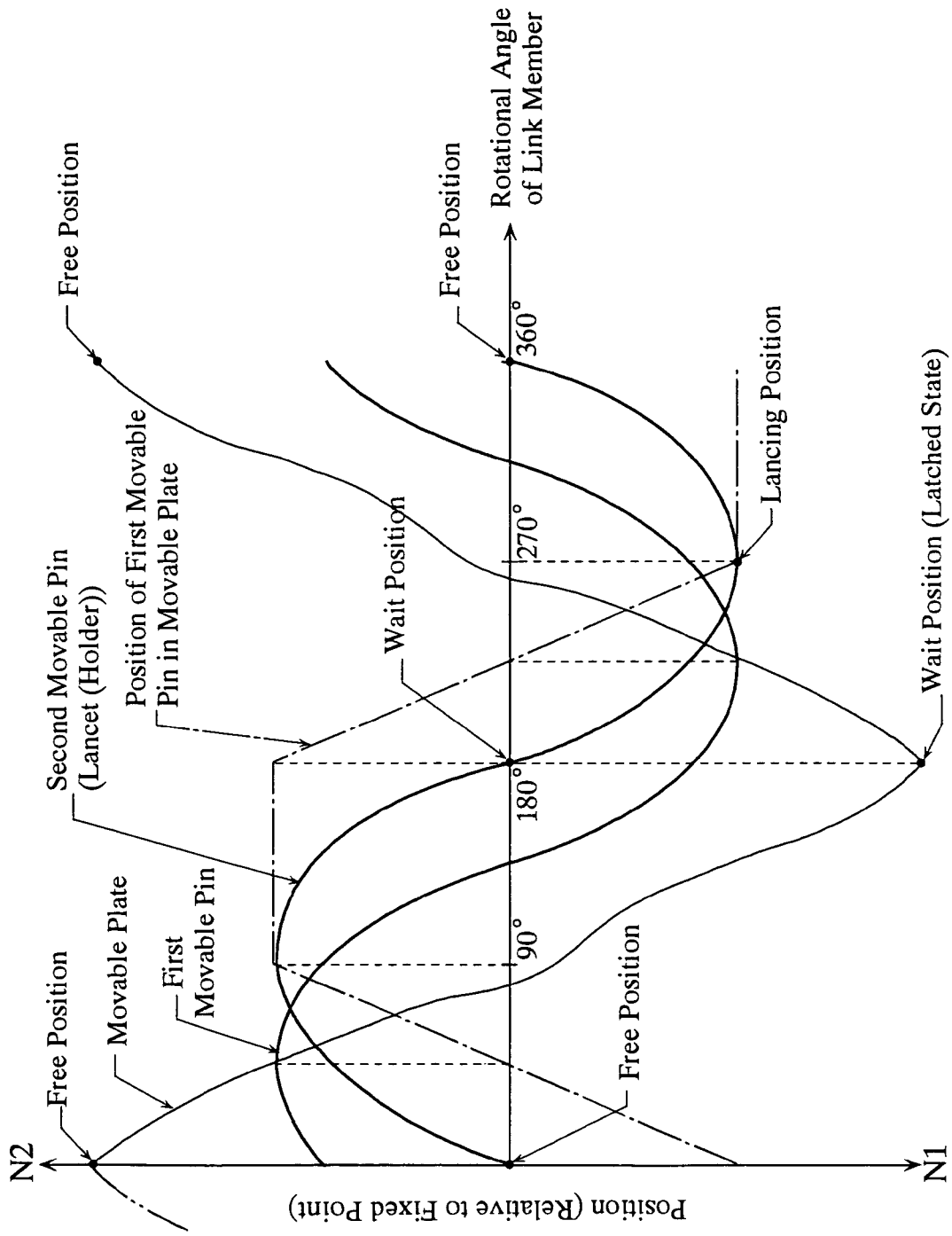
FIG. 16 is a graph showing change of position of the movable plate and the lancet holder in the lancing operation.

As shown in FIG. 5, in the link member 30, the positional relationship between the pins 30a-30c is defined by the connection of the pins 30a-30c with each other via the first and the second arms 30A and 30B. Specifically, the first and the second movable pins 30a and 30b are equal to each other in distance to the fixing pin 30c, while the second movable pin 30b is deviated 45 degrees relative to the first movable pin 30a on a circumference around the fixing pin 30c as the center. Therefore, when the link member 30 is rotated around the fixing pin 30c as the rotation center, the first and the second movable pins 30a and 30b perform circular motion around the fixing pin 30c. As shown in FIG. 16, respective routes of the first and the second movable pins 30a and 30b in a lancing direction N1 and a retreating direction N2 are depicted as sine curves 45-degree phase shifted from each other.

As shown in FIGS. 6A and 6B, the movable plate 31 is movable relative to the housing 2 in the lancing direction N1 and the retreating direction N2 and connected to the housing 2 via a coil spring Sp. The movable plate 31 includes a groove 31A, the actuating portion 31B and a hook 31C.

The groove 31A serves to allow the movement of the first movable pin 30a of the link member 30 (See FIG. 3). The groove 31A includes an inclined groove portion 31Aa extending in a direction inclined with respect to the lancing and retreating directions N1, N2, and straight groove portions 31Ab connected to opposite ends of the inclined groove portion 31Aa. As will be understood from FIGS. 15A-15D and 16, the first movable pin 30a moves along the inclined groove portion 31Aa at least when the lancet 1 moves from the wait position toward the lancing position and moves along the straight groove portions 31Ab at least when the lancet 1 moves from the lancing position in the retreating direction N2.

With the provision of the above groove 31A, the position of the movable plate 31 in the housing 2 is determined based on the position of the first movable portion 30a itself in the lancing and the retreating directions N1, N2 and the position of the movable portion 30a in the groove 31A. Specifically, as shown in FIG. 16, the position of the movable plate 31 is obtained as the difference between the position of the first movable portion 30a in the lancing and the retreating directions N1, N2 with respect to the fixing pin 30c as the reference and the position of the first movable portion 30a in the groove 31A in the lancing and the retreating directions N1, N2 with respect to the center of the groove 31a as the reference.

Therefore, in the case where the link member 30 is rotated clockwise, during when the link member 30 makes one rotation, the movable plate 31 reciprocates between a free position (top dead center) and a latch position (bottom dead center), with the fixing pin 30c set as the center.

As shown in FIGS. 6A and 6B, the actuating portion 31B is used to manually move the movable plate 31. The actuating portion 31B partially projects outward through the first opening 21b of the housing 2 and is allowed to move through the first opening 21b in the lancing and the retreating directions N1 and N2.

The hook 31C serves to engage the projection 21a of the housing 2 to latch the movable plate 31 to the housing 2. As better shown in FIG. 6B, when the coil spring Sp is compressed, the hook 31C of the movable plate 31 is positioned on the retreated side N2 of the projection 21a. As better shown in FIG. 6A, when the hook 31C engages the projection 21a, the coil spring Sp is expanded and biased in the retreating direction N2.

Figure 7:
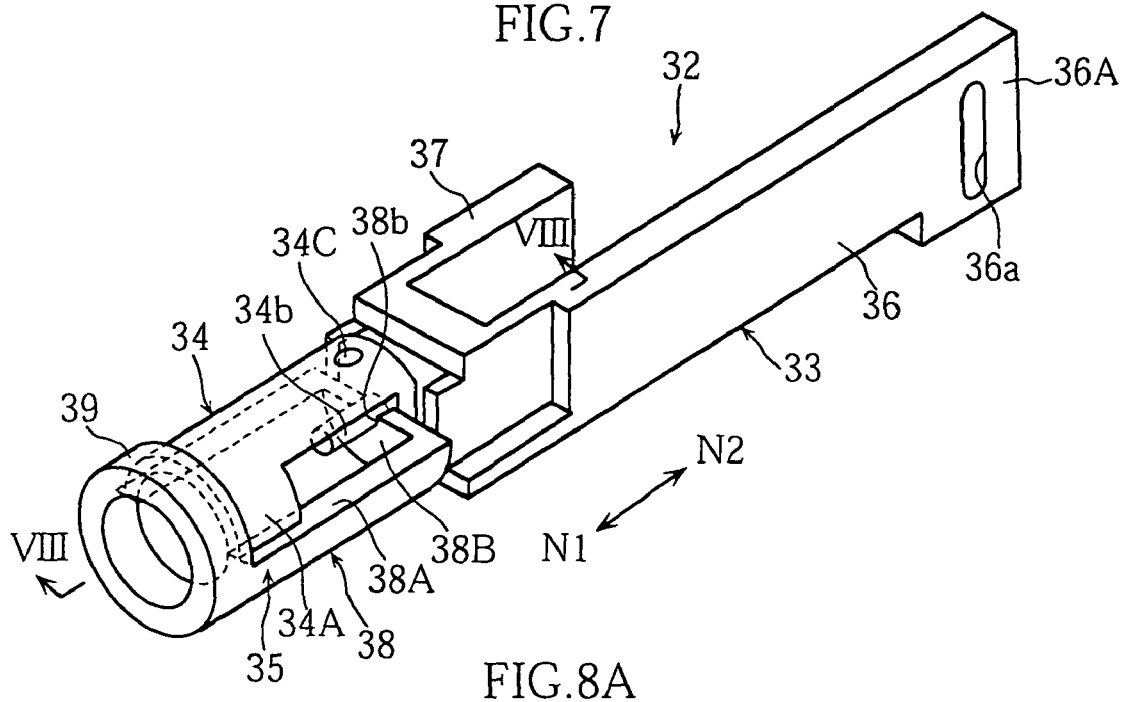
FIG. 7 is an entire perspective view of a lancet holder.

As shown in FIGS. 7 and 8, the lancet holder 32, which serves to hold and move the lancet 1 (see FIG. 1), is movable in the lancing and the retreating directions N1 and N2, similarly to the movable plate 31 (See FIG. 6). The lancet holder 32 includes a first and a second members 33 and 34 which are movable relative to each other.

Figure 8A:
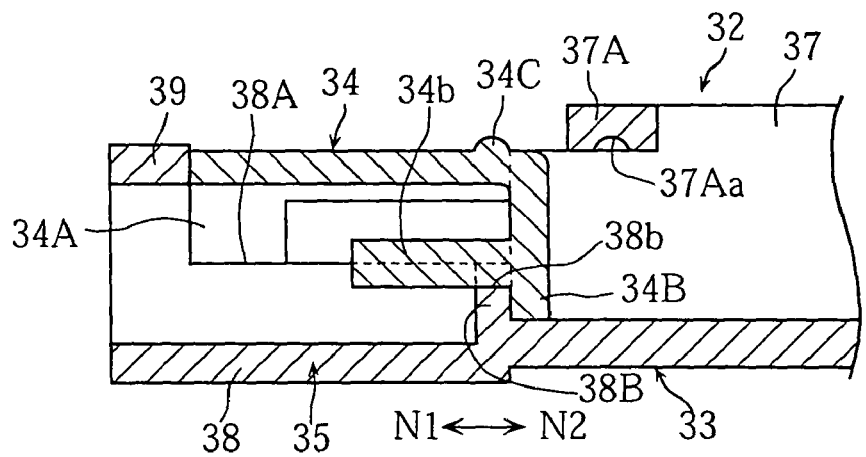
FIG. 8A is a sectional view taken along lines VIII-VIII in FIG. 7.
Figure 8B:
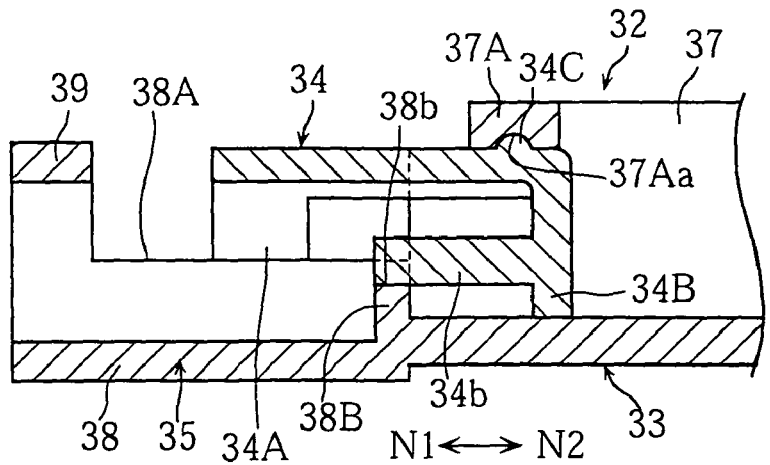
FIG. 8B is a sectional view showing the state in which the second member of the lancet holder shown in FIG. 8A is moved.
Figure 9:
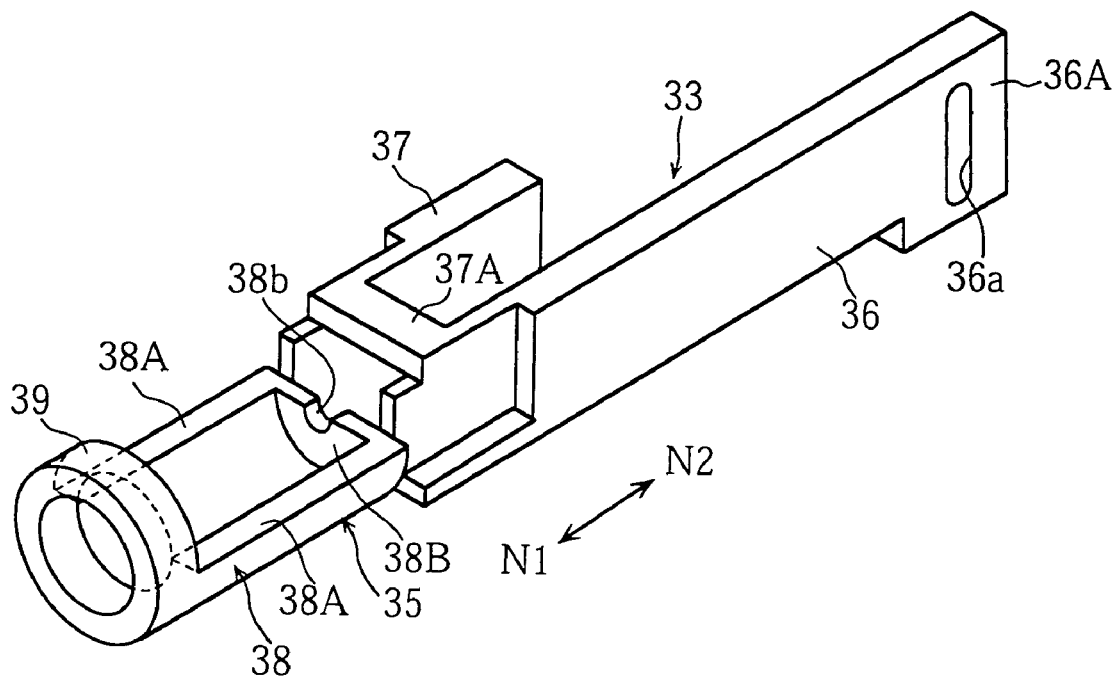
FIG. 9 is an entire perspective view showing the first member of the lancet holder of FIG. 7.

As shown in FIGS. 7-9, the first member 33 includes a holder portion 35 for holding the lancet 1 (See FIG. 1), a first plate portion 36 connected to the movable plate 31 via the link member 30 (See FIGS. 3-5), and a second plate portion 37 facing the first plate portion 36.

The holder portion 35 includes an accommodation portion 38 for accommodating the lancet 1 (See FIG. 1), and a restricting portion 39 for restricting the movement of the lancet 1 (See FIG. 1) in the radial direction. The accommodation portion 38 is shaped like a half pipe having an inner surface configuration conforming to the outer surface configuration of the lancet 1, and includes a pair of guide surfaces 38A and a wall 38B. As will be understood from FIGS. 8A and 8B, the guide surfaces 38A guide the movement of an arch portion 34A of the second member 34, which will be described later. The wall 38B is formed with a cutout 38b for guiding the movement of a pin 34b of the second member 34, which will be described later. As shown in FIG. 9, the cutout 38b is formed into a semicircular shape at an end of the accommodation portion 38. The restricting portion 39 is continuously connected to the holder portion 35 and has an inner diameter corresponding to the outer diameter of the lancet 1 (See FIG. 1).

The first plate portion 36 extends in the lancing and the retreating directions N1 and N2, and is formed with a groove 36a at an end 36A. As will be perceived from FIGS. 1 and 3, the groove 36a serves to allow the movement of the second movable pin 30b of the link member 30 and extends in a direction perpendicular to the lancing and the retreating directions N1 and N2. Therefore, as will be understood from FIGS. 15A-15D and 16, the position of the first plate portion 36 (the lancet holder 32) corresponds to the position of the second movable pin 30b in the lancing and the retreating directions N1 and N2. Therefore, during when the link member 30 makes one rotation, the lancet holder 32 makes one cycle of reciprocal movement, with the fixing pin 30c set as the center.

As shown in FIGS. 8 and 9, the second plate portion 37, along with the first plate portion 36, guides a pusher 50 (See FIGS. 14A and 14B) of the lancet discharge mechanism 5, which will be described later. The second plate portion is connected to the first plate portion 36 via a connection portion 37A. The connection portion 37A is formed with a recess 37Aa for engaging a projection 34C of the second member 34, which will be described later.

As shown in FIGS. 8A and 8B, the second member 34 is movable in the lancing or the retreating direction N1, N2 in mounting the lancet 1 (See FIG. 1) and by the action of the lancet discharge mechanism 5. The second member includes the arch portion 34A and a stopper portion 34B.

Figure 10:
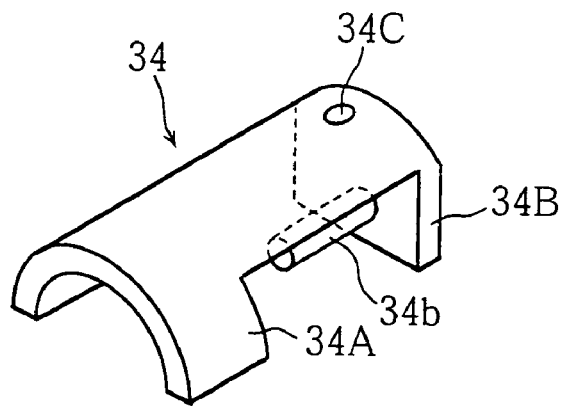
FIG. 10 is an entire perspective view showing the second member of the lancet holder of FIG. 7.

As shown in FIG. 10, the arch portion 34A has a semi-cylindrical shape to cover the outer surface of the lancet 1 (See FIG. 1), and is arranged to bridge the guide surfaces 38A of the first member 33, as shown in FIGS. 7, 8A and 8B.

As shown in FIGS. 8A and 8B, when the second member 34 is moved relative to the first member 33 in the lancing direction N1, the stopper portion 34B comes into contact with the wall 38B of the first member 33 to restrict the movement of the second member 34 relative to the first member 33 in the lancing direction N1. The stopper portion 34B is provided with a pin 34b projecting in the lancing direction N1. The pin 34b engages the lancet 1 (See FIG. 1) in mounting the lancet 1 (See FIG. 1) to the lancet holder 32. The movement of the pin is guided by the cutout 38b formed at the wall 38B of the first member 33.

The second member 34 is formed with a hemispherical projection 34C adjacent the stopper portion 34B. The projection 34C is to be fitted in the recess 37Aa of the connection portion 37A of the first member 33 and is made slightly larger than the recess 37Aa. When the lancet 1 is inserted until it comes into contact with the wall 38B of the first member 33, the projection 34C fits into the recess 37Aa. Since the projection 34C is slightly larger than the recess 37Aa, when the projection 34C is fitted into the recess 37Aa, a force to press the lancet 1 is exerted on the arch portion 34A. Therefore, by fitting the projection 34C into the recess 37Aa, the lancet 1 (See FIG. 1) is sandwiched between the arch portion 34A and the accommodation portion 38, with the pressing force exerted on the lancet 1. Therefore, the lancet 1 (See FIG. 1) can be reliably held by the lancet holder 32. When the projection 34C is released from the recess 37Aa, the force to press the lancet 1 by the arch portion 34A is reduced, so that the lancet 1 (See FIG. 1) can be easily removed from the lancet holder 32.

Figure 11:
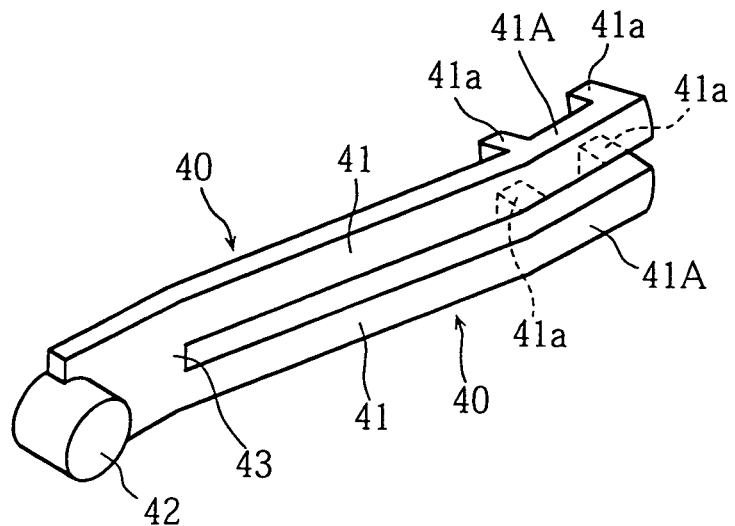
FIG. 11 is an entire perspective view showing a swayable member of a latch release mechanism of the lancing apparatus shown in FIG. 1.
Figure 12:
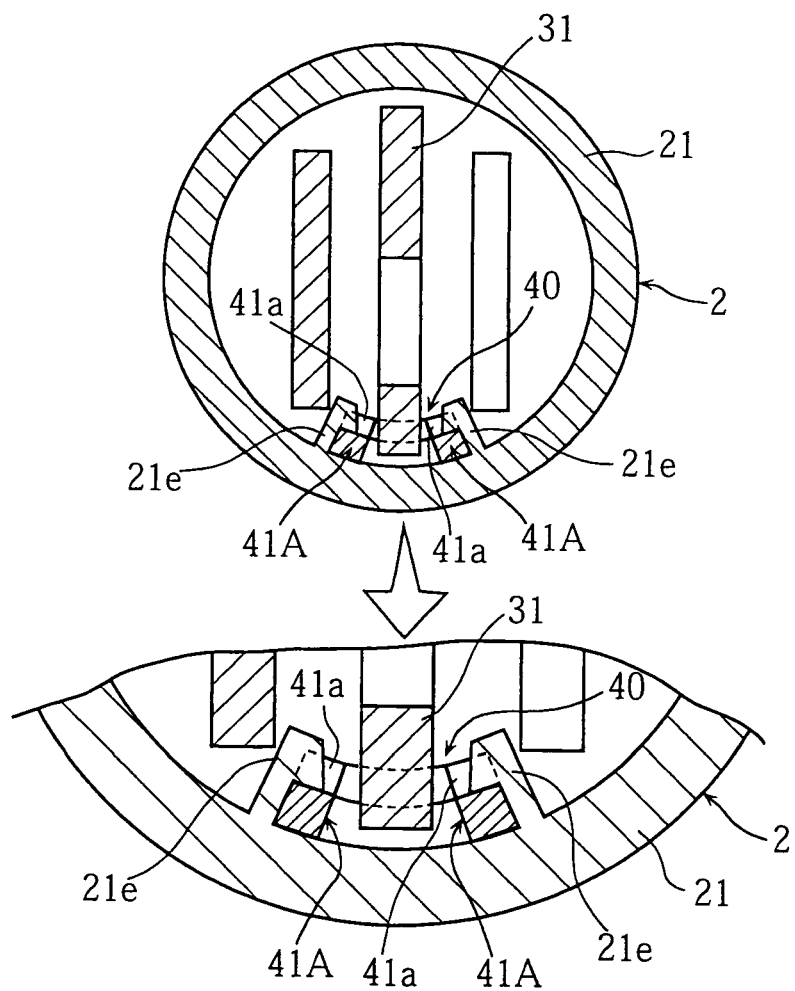
FIG. 12 is a sectional view for describing the fixed state of the swayable member, the principal part of which is shown as enlarged.

As shown in FIGS. 6A and 6B, the latch release mechanism 4 serves to release the latched state of the movable plate 31 relative to the housing 2, and includes a swayable member 40. As shown in FIG. 11, the swayable member 40 includes a pair of spring portions 41, the press portion 42 and an operative portion 43.

The paired spring portions 41 have appropriate resiliency and extend from the operative portion 43. As will be perceived from FIGS. 11 and 12, the paired spring portions 41 are spaced from each other by a predetermine distance so that the hook 31C (See FIGS. 6A and 6B) of the movable plate 31 can move between the spring portions 41. Each spring portion 41 has an end formed with a fixing portion 41A. The fixing portion 41A is utilized for fixing the swayable member 40 to the housing 2. The fixing portion 41A includes a pair of projections 41a and engages, between the projections 41a, with an engagement piece 21e provided at the first sleeve 21 of the housing 2.

Figure 13A:
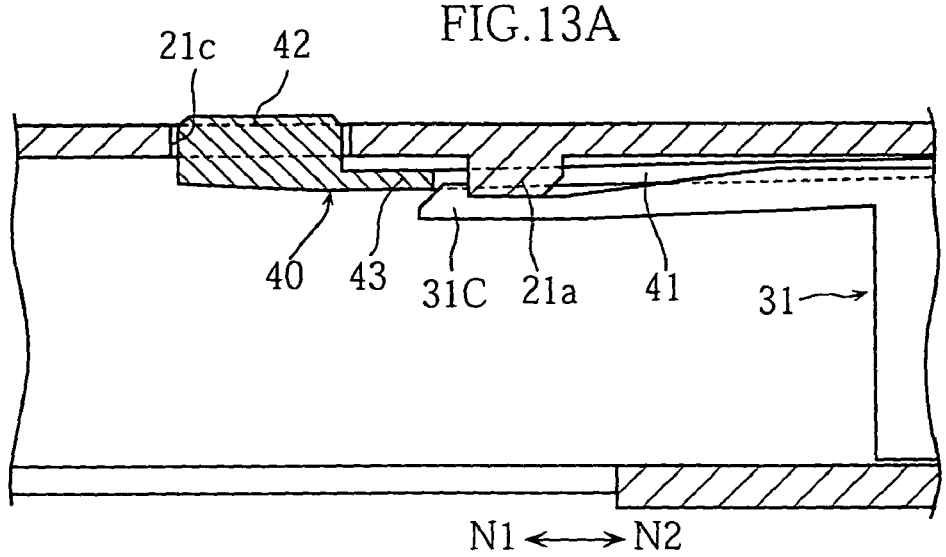
FIGS. 13A-13C are sectional views showing the principal part of the latch release mechanism for describing the operation, in which part of the structural elements is omitted.
Figure 13B:
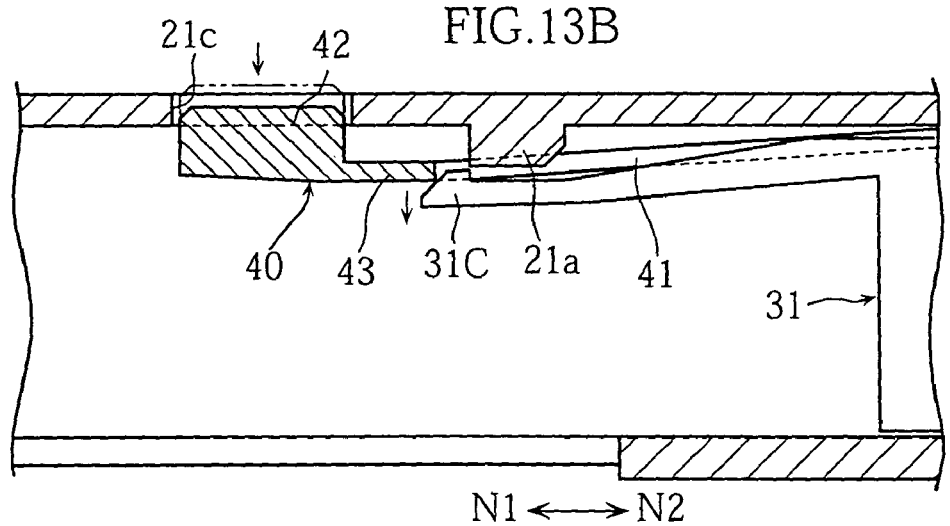
Figure 13C:
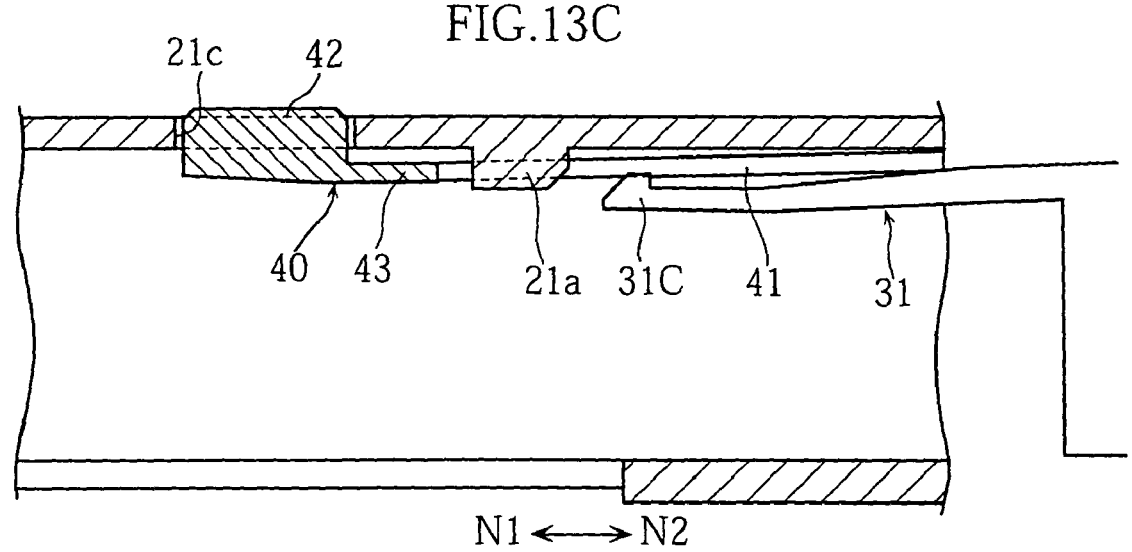

The press portion 42 is a portion to be pressed by the user. As shown in FIGS. 13A-13C, by pressing the press portion 42, the engagement of the hook 31C of the movable plate 31 can be released. The press portion 42 is exposed through the second opening 21c of the housing 2 and allowed to move through the second opening 21c. Since the swayable member 40 is fixed to the housing 2 at the fixing portion 41A (See FIG. 12) and the spring portions 41 have appropriate resiliency, the press portion 42, along with the operative portion 43, can sway about the fixing portion 41A serving as the fulcrum.

The operative portion 43 serves to exert a pressing force on the hook 31C when the press portion 42 is pressed. As shown in FIGS. 13B and 13C, when the pressing force is exerted, the hook 31C moves toward the inner side of the housing 2, whereby the hook 31C is disengaged. As noted before, when the hook 31C is engaged with the projection 21a, the movable plate 31 is biased toward the retreating direction N2. Therefore, as shown in FIG. 6B, by disengaging the hook 31C, the movable plate 31 moves in the retreating direction N2.

As shown in FIG. 14, the lancet discharge mechanism 5 serves to remove the lancet 1 from the lancet holder 32 after the lancing operation. The lancet discharge mechanism 5 includes the pusher 50 which is movable in the lancing and the retreating directions N1 and N2 relative to the housing 2 and the lancet holder 32. The pusher 50 includes an actuating portion 51 and an operative portion 52. The actuating portion 51 is used by the user to manually move the pusher 50 and allowed to move through the third opening 21d in the lancing and the retreating directions N1 and N2. The operative portion 52 serves to engage the stopper portion 34B of the second member 34 of the lancet holder 32. When the actuating portion 51 is moved in the lancing direction N1, the operative portion moves between the first and the second plate portions 36 and 37 of the lancet holder 32 in the lancing direction N1. Therefore, in the lancet discharge mechanism 5, by moving the actuating portion 51 in the lancing direction N1, the operative portion 52 can be moved in the lancing direction N1 to move the second member 34 of the lancet holder 32. By the movement of the second member 34, the pin 34b of the second member 34 moves in the lancing direction N1, and the pin 34b moves the lancet 1 in the lancing direction N1.

The usage and operation principle of the lancing apparatus X1 will be described. It is to be noted that the following description is given on the assumption that, in the initial state, the movable plate 31 is positioned at a free position (top dead center) of the retreating direction N2, the first movable pin 30a is positioned at the left end of the inclined groove portion 31Aa of the groove 31A of the movable plate 31, and the second movable pin 30b is positioned at the left end of the groove 36a of the lancet holder 32, as shown in FIGS. 15A and 16. The rotation angle of the link member 30 in this state is defined as 0 degree.

First, to lance the skin by using the lancing apparatus X1, the lancet 1 is mounted to the lancet holder 32 after the hook 31C of the movable plate 31 is engaged with the projection 21a of the housing 2, as shown in FIGS. 1 and 15C. Alternatively, the movable plate 31 may be latched to the housing 2 after the lancet 1 is mounted to the lancet holder 32.

As shown in FIGS. 15A-15C, the engagement of the hook 31C can be performed by moving the actuating portion 31B of the movable plate 31 in the lancing direction N1.

When the movable plate 31 is moved in the lancing direction N1 from the state shown in FIG. 15A, the first movable pin 30a of the link member 30 tries to move to the right side through the inclined groove portion 31Aa of the movable plate 31, as shown in FIGS. 15A and 15B. To allow such movement of the first movable pin 30a, the entirety of the link member 30 including the second movable pin 30b tries to rotate clockwise around the fixing pin 30c. To allow such rotation of the link member 30, the second movable pin 30b moves toward the center of the groove 36a of the lancet holder 32 while lifting the lancet holder 32 in the retreating direction N2. Therefore, when the movable plate 31 is moved from the position shown in FIG. 15A to the position shown in FIG. 15B (rotation angle of the link member 30 is in the range of 0° to 90°), the lancet holder 32 moves in the retreating direction N2 in accordance with the movement of the movable plate 31 in the lancing direction N1.

When the movable plate 31 is further moved from the state shown in FIG. 15B in the lancing direction N1, the first movable pin 30a of the link member 30 tries to reciprocate along the straight portion 31Ab of the groove 31, as shown in FIGS. 15B and 15C. To allow such movement of the first movable pin 30a, the second movable pin 30b moves through the groove 36a from the center to the right while pushing down the lancet holder 32 in the lancing direction N1. Therefore, when the movable plate 31 is moved from the position shown in FIG. 15B to the position shown in FIG. 15C (rotation angle of the link member 30 is in the range of 90° to 180°), the lancet holder 32 moves in the lancing direction N1 in accordance with the movement of the movable plate 31 in the lancing direction N1. When the movable plate 31 is moved a predetermined distance in the lancing direction N1, the hook 31C of the movable plate 31 engages the projection 21a of the housing 2, as shown in FIG. 15C. Since the coil spring Sp is expanded, the movable plate 31 is latched to the housing 2 while being biased in the retreating direction N2.

Figure 2:
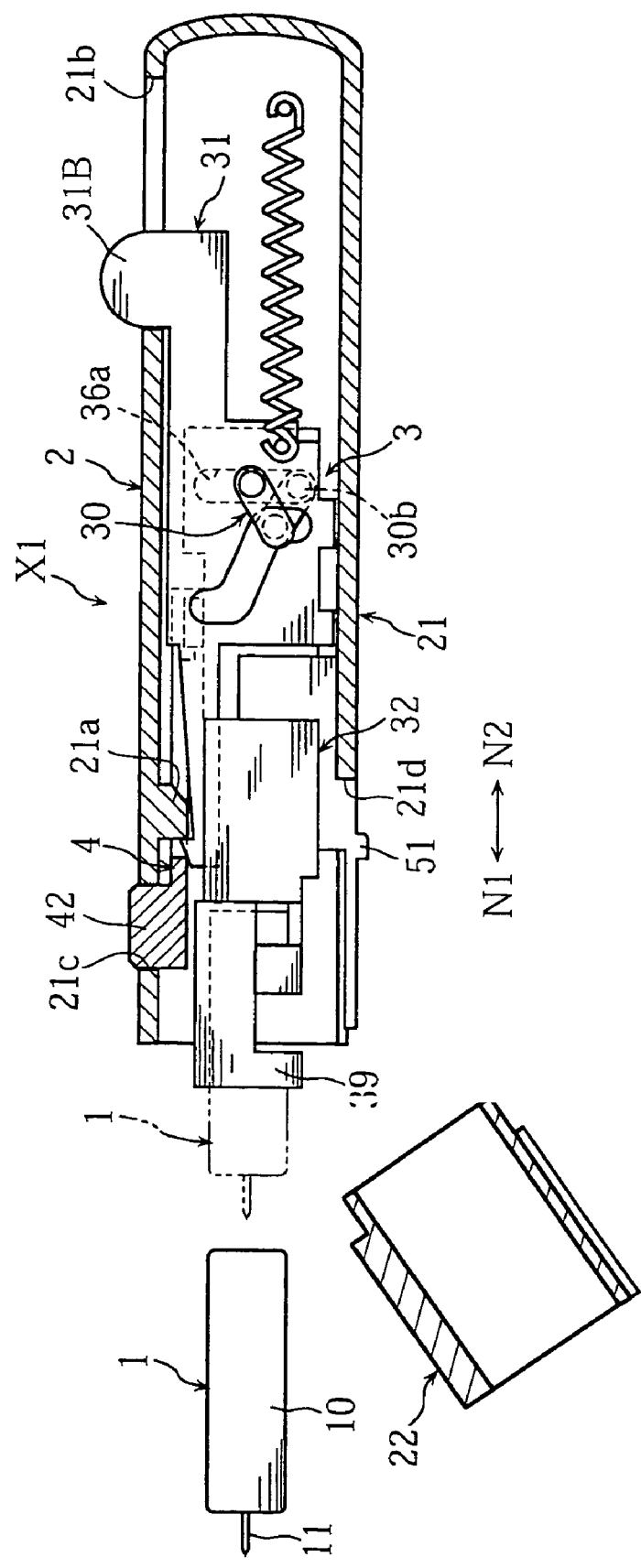
FIG. 2 is a sectional view of the lancing apparatus shown in FIG. 1 in the state in which the second sleeve and the lancet are removed.

To mount the lancet 1, the second sleeve 22 is removed from the first sleeve 21 to expose the restricting portion 39 of the lancet holder 32 at the first sleeve 21, as shown in FIG. 2. Subsequently, the lancet 1 is inserted through the restricting portion 39 from the end opposite from the lancing needle 11. As shown in FIG. 14B, the end surface of the lancet 1 comes into contact with the pin 34b of the second member 34, and the second member 34 along with the pusher 50 of the lancet discharge mechanism 5 moves in the retreating direction N2. When the second member 34 is moved a predetermined distance, the end surface of the lancet 1 comes into contact with the stopper portion 38B of the first member 33, whereby further movement of the lancet 1 in the retreating direction N2 is prevented. At this time, the projection 34C of the second member 34 fits into the recess 37Aa of the first member 33. As a result, the second member 34 is pressed against the first member 33 so that the lancet 1 is sandwiched between the first and the second members 33 and 34. In this way, the lancet 1 is reliably held by the lancet holder 32.

After the latching of the movable plate 31 and the mounting of the lancet 1 are completed, lancing of the skin is performed by pressing the press portion 42 of the latch release mechanism 4, as shown in FIGS. 6A, 6B and 13A-13D. When the press portion 42 is pressed, the swayable member 40 including the press portion 42 and the operative portion 43 moves toward the inner side of the housing 2, with the fixing portion 41A serving as the fulcrum. As a result, as shown in FIG. 13B, the operative portion 43 engages the hook 31C to move the hook 31 toward the inner side, whereby the hook 31C is disengaged from the projection 21a.

Since the movable plate 31 is biased toward the retreating direction N2 as noted above, the movable plate 31 tries to move toward the retreating direction N2, as shown in FIGS. 15C and 15D. At this time, the first movable pin 30a of the link member 30 tries to move through the inclined groove portion 31Aa of the movable plate 31 to the left. To allow such movement of the first movable pin 30a, the entirety of the link member 30 including the second movable pin 30b tries to rotate clockwise around the fixing pin 30c. To allow such rotation of the link member 30, the second movable pin 30b moves through the groove 36a of the lancet holder 32 from the right side toward the center, while pushing down the lancet holder 32 in the lancing direction N1. (The rotation angle of the link member 30 in FIG. 16 is in the range of 180° to 270°.)

As shown in FIG. 15D, by the movement of the lancet holder 32 in the lancing direction N1, the lancet 1 also moves in the lancing direction N1 and lances the skin Sk. Since the coil spring Sp is expanded as compared with the state shown in FIG. 15A, the movable plate 31 further tries to move in the retreating direction N2. To allow such movement of the movable plate 31, the second movable pin 30b moves through the groove 36a from the center to the left, while the link member 30 rotates clockwise around the fixing pin 30c so that the first movable pin 30a reciprocate along the straight portion 31Ab of the groove 31A. By this movement, the lancet holder 32 is lifted in the retreating direction N2. Thus, the lancet holder 32 returns to the free position before the latching, whereby the lancet 1 is pulled out from the skin, as shown in FIG. 15A. (The rotation angle of the link member in FIG. 16 is in the range of 270° to 360°.)

After the lancing operation is completed, the lancet 1 is removed from the lancet holder 32. The removal of the lancet 1 is performed by utilizing the lancet discharge mechanism 5, as shown in FIGS. 14A and 14B. Specifically, the lancet 1 is removed from the lancet holder 32 by moving the actuating portion 51 of the lancet discharge mechanism 5 in the lancing direction N1.

When the actuating portion 51 is moved in the lancing direction N1, the operative portion 52 moves in the lancing direction N1 to engage the stopper portion 34B. When the actuating portion 51 is further moved from this state in the lancing direction N1, a force in the lancing direction N1 is exerted on the stopper portion 34B via the operative portion 52. When a force greater than a predetermined level is exerted on the stopper portion 34B, the projection 34C of the second member 34 fitted in the recess 37Aa of the first member 33 disengages from the recess, so that the second member 34 moves in the lancing direction N1. As a result, the pin 34b of the second member 34 pushes the end surface of the lancet 1, whereby the lancet 1 moves in the lancing direction N1. Since the projection 34C is disengaged from the recess 37Aa, the force to press the lancet 1 by the arch portion 34A of the second member 34 is reduced, so that the lancet 1 can be easily removed from the lancet holder 32.

In the lancing apparatus X1, the movable plate 31 can be easily latched to the housing 2 by pushing down the actuating portion 31B of the movable plate 31. Further, the lancing of the skin can be performed just by pressing the press portion 42 of the latch release mechanism 4. In this way, the lancing can be performed by extremely easy operations of pushing down the actuating portion 31B and pressing the press portion 42, so that the lancing apparatus X1 is easy to use.

In the lancing apparatus X1, by releasing the latched state, the lancing needle 11 is reciprocated between the wait position and the lancing position in accordance with the circular motion of the link member 30, which provides the following advantages.

Firstly, the lancing needle 11 can be pulled out from the skin immediately after the lancing needle 11 sticks in the skin. Therefore, the period of time during which the lancing needle 11 sticks in the skin is relatively short, so that pain given to the patient can be reduced.

Figure 34A:
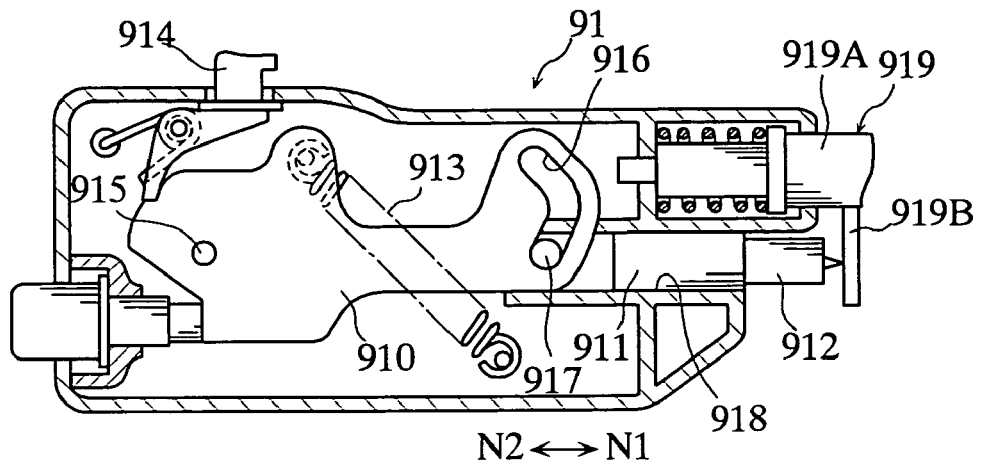
FIGS. 34A-34C are sectional views showing another example of prior art lancing apparatus.
Figure 34B:
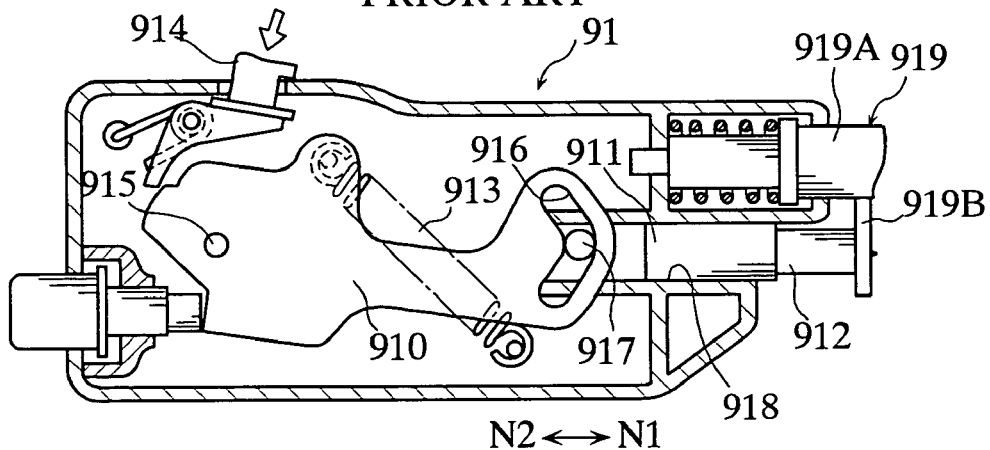
Figure 34C:
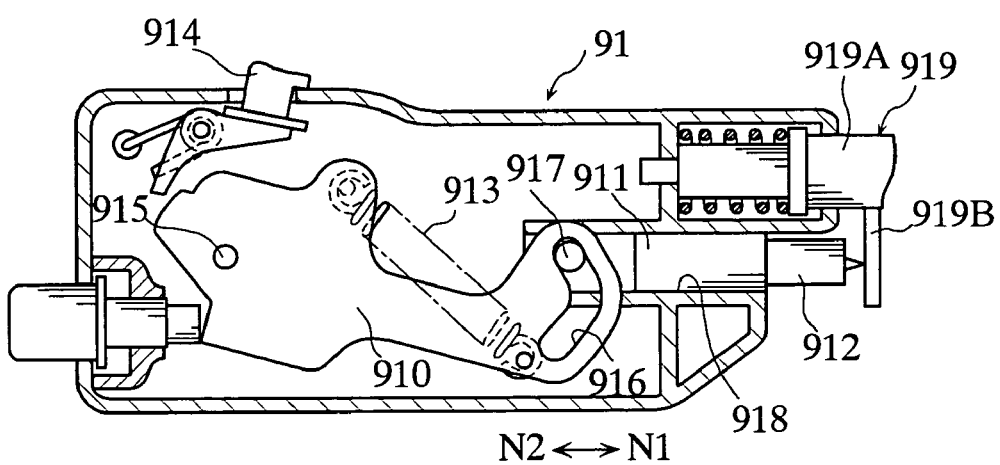
Figure 35:
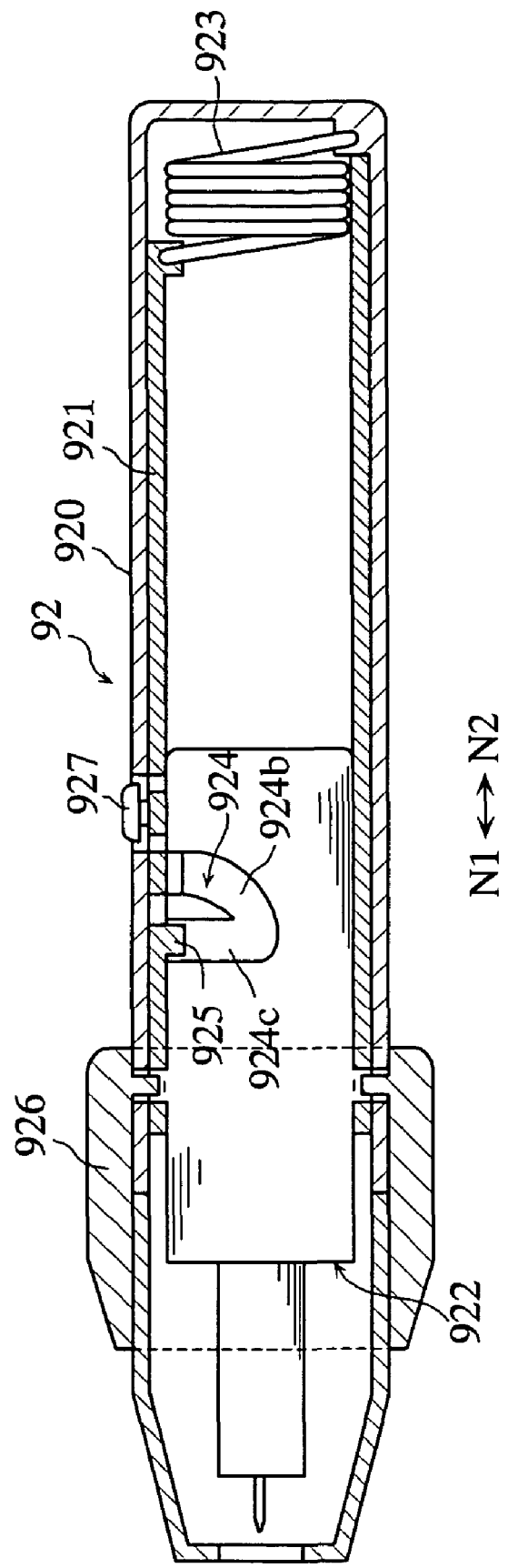
FIG. 35 is a sectional view showing another example of prior art lancing apparatus.
Figure 36:
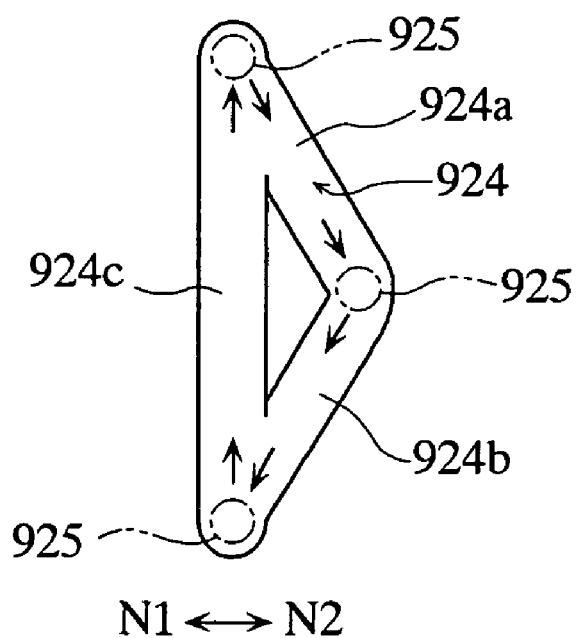
FIG. 36 is a plan view of the principal part of the lancing apparatus shown in FIG. 35 for describing the driving cam of the apparatus.

Secondly, since the lancing needle 11 is retreated after sticking in the skin, the lancing needle 11 is not left projecting from the housing 2, which provides safety. In the lancing apparatus X1, the retreat of the lancing needle 11 can be realized by a simple structure without utilizing a mark member 919 provided in the prior-art lancing apparatus 91 described with reference to FIGS. 34A-34C. Therefore, the manufacturing cost of the lancing apparatus can be reduced.

Thirdly, the impact, impact noise and vibration in the lancing, and further, the shaking of the lancing needle 11 can be suppressed, so that pain or discomfort given to the patient can be reduced. Specifically, since the lancet holder 32 does not hit against the housing 2 when the lancing needle 11 reaches the lance position, impact and impact noise are not generated. Therefore, the discomfort in lancing can be reduced. Further, the lancet holder 32 is reciprocated by the rotation of the link member 30. Therefore, when the lancet holder 32 moves, a force to control the movement of the lancet holder 32 is constantly exerted on the lancet holder 32. Therefore, the lancet holder 32 can be moved properly in the directions N1 and N2 even if any engagement or friction occurs between the inner surface of the housing 2 and the lancet holder 32 during the movement. Accordingly, in the lancing apparatus X1, the gap between the link member 30 and the lancet holder 32, and the housing 2 can be made relatively small, which suppresses the shaking of the lancet holder 32 during the movement. Further, as will be understood from FIG. 16, in the lancing apparatus X1, the movable plate 31 moves in the retreating direction N2 when the lancet holder 32 (lancet 1) moves from the wait position to the lancing position. Therefore, the vibration generated when the lancet 1 moves in the lancing direction N1 to reach the lancing position can be compensated for by the movement of the movable plate 31 in the retreating direction N2. As a result, unnecessary impact on the lancet 1 can be prevented.

The lancing apparatus according to the first embodiment of the present invention is not limited to the above-described example and may be modified in various ways. For instance, although the movable plate 31 is latched to the housing 2 by moving in the lancing direction N1 in the above example, the movable plate 31 may be latched to the housing 2 by moving in the retreating direction N2. In this case, the lancet holder 32 is designed to reciprocate by moving the movable plate 31 in the lancing direction N1.

In this embodiment, description is made of the example in which the reciprocal movement of the movable plate 31 and that of the lancet holder 32 are 90-degree phase shifted from each other. However, the phase shift during the movement of the movable plate 31 and the lancet holder 32 is not limited to 90 degrees. The positional relationship between the first and the second movable pines 30a and 30b of the link member 30 or the configuration of the groove 31A of the movable plate 31 and that of the groove 36a of the lancet holder 32 are not limited to the illustrated example of this embodiment. Further, even when the phase shift during the movement of the movable plate 31 and the lancet holder 32 is set to 90 degrees, the positional relationship between the first and the second movable pines 30a and 30b of the link member 30 and the configuration of the groove 31A of the movable plate 31 and that of the groove 36a of the lancet holder 32 are not limited to the illustrated example of this embodiment.

To alleviate the impact and vibration in stopping the movable plate 31 and the lancet holder 32, the movable plate 31 and the lancet holder 32 may be stopped while braking, instead of stopping suddenly. Specifically, when the movable plate 31 and the lancet holder 32 come close to the stop position, the movable plate 31 and the lancet holder 32 may be caused to come into contact with the housing 2 (first sleeve 21) so that the movable plate 31 and the lancet holder 32 stop while braking due to the frictional force. The frictional force may be generated by providing the housing 2 (first sleeve 21) with a projection at or around the portion where the movable plate 31 and the lancet holder 32 are to be stopped or by reducing the inner diameter at that portion of the housing 2 (first sleeve 21). Instead of modifying the design of the housing 2 (first sleeve 21), a projection or the like may be provided at the movable plate 21 and the lancet holder 32 to reliably generate a frictional force.

Next, a second embodiment of the present invention will be described with reference to FIGS. 17-24. In FIGS. 17-24, the elements which are identical or similar to those of the foregoing lancing apparatus X1 are designated by the same reference signs as those used for the foregoing lancing apparatus.

Figure 17:
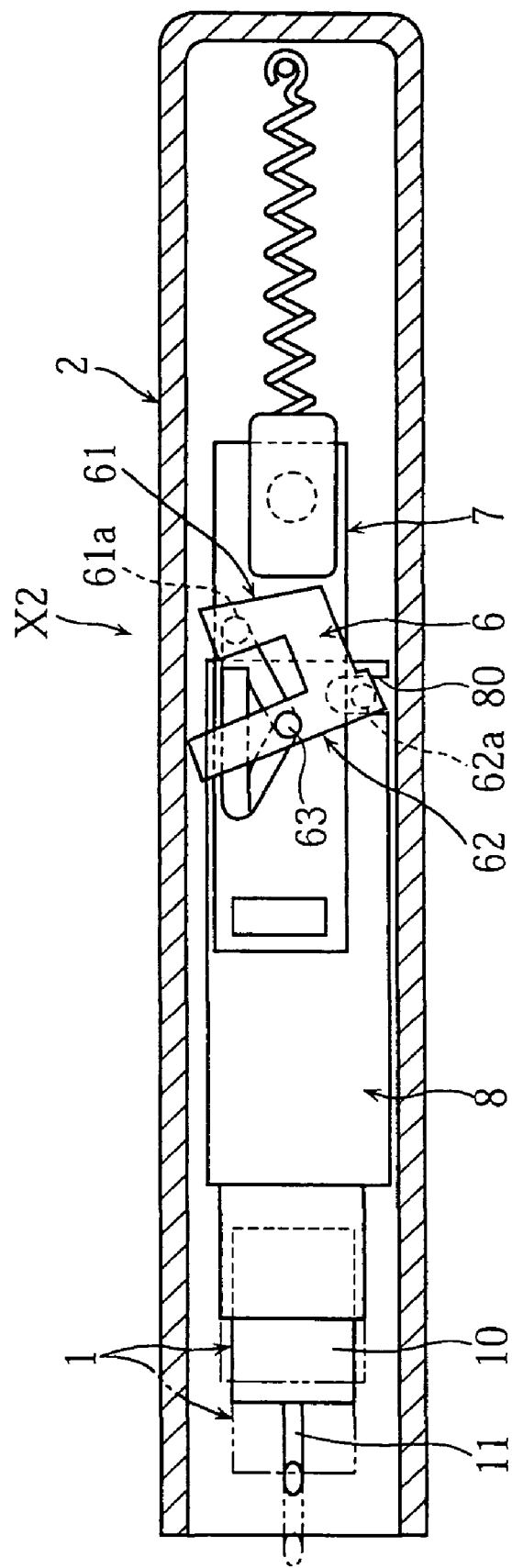
FIG. 17 is a sectional view showing a lancing apparatus according to a second embodiment of the present invention.
Figure 18:
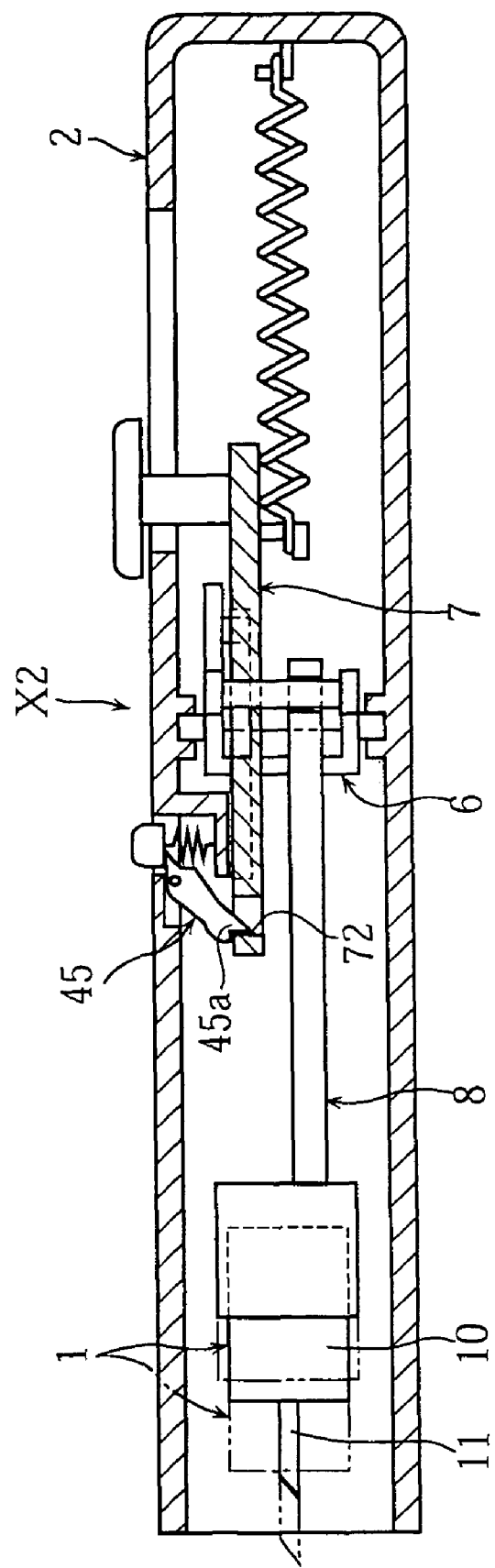
FIG. 18 is another sectional view of the lancing apparatus of FIG. 17.

As shown in FIGS. 17 and 18, in the lancing apparatus X2, the link member 6, the movable plate 7 and the lancet holder 8 are accommodated in the housing 2. By pivoting the link member 6, the movement of the movable plate 7 is converted into reciprocal movement of the lancet holder 8.

Figure 19:
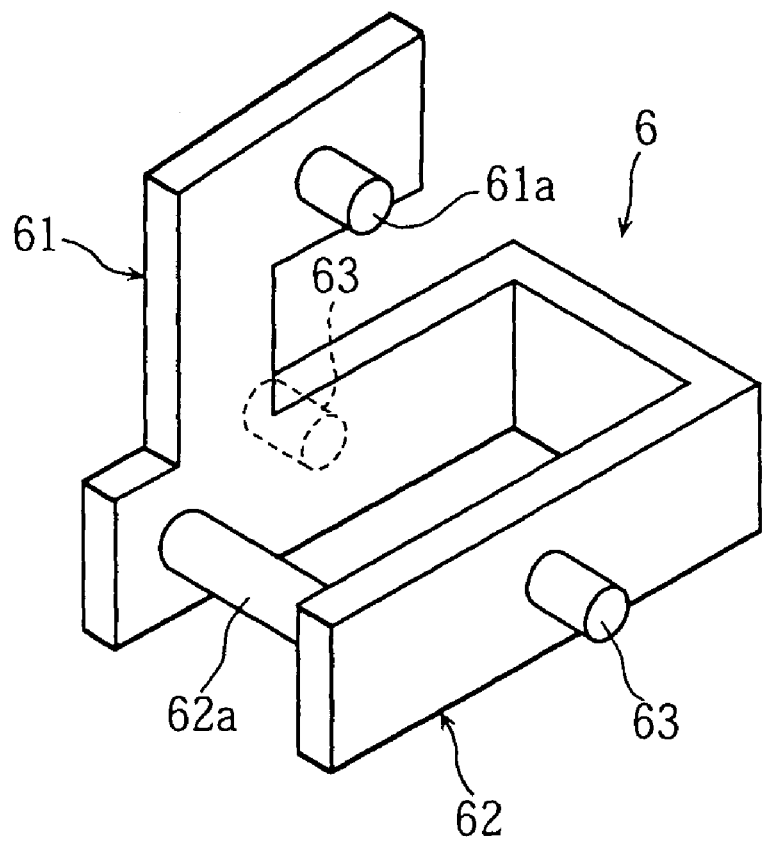
FIG. 19 is an entire perspective view of the link member of the lancing apparatus shown in FIGS. 17 and 18.

As shown in FIGS. 17 and 19, the link member 6, whose movement is controlled by the movable plate 7, controls the movement of the lancet holder 8. The link member 6 includes a fist arm 61 and a second arm 62.

The first arm 61 includes a pivot pin 61a. The pivot pin 61a engages a cam groove 70 of the movable plate 7, which will be described later. The second arm 62 includes a pivot pin 62a. The second pin 62a engages a cutout 80 of the lancet holder 8, which will be described later. The second arm 62 is provided with a rotation pin 63. The rotation pin 63 is rotatably fixed to the housing 2. The pivot pins 61a and 62a are rotatable around the rotation pin 63.

Figure 21:
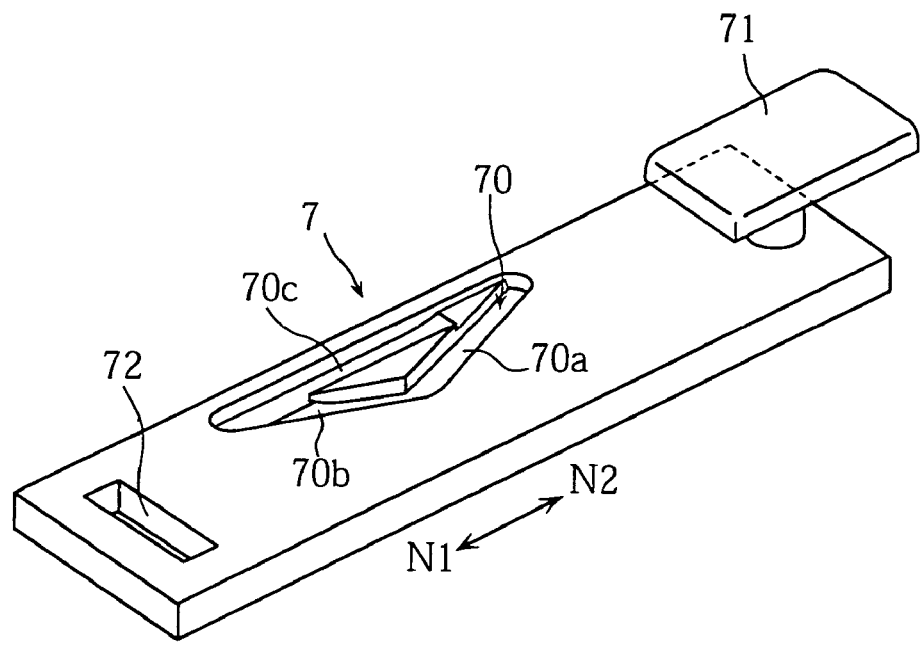
FIG. 21 is an entire perspective view of the movable plate of the lancing apparatus shown in FIGS. 17 and 18.

As shown in FIGS. 20A and 20B, the movable plate 7 is movable relative to the housing 2 in the lancing direction N1 and the retreating direction N2 and connected to the housing 2 via a coil spring Sp. As shown in FIG. 21, the movable plate 7 includes the cam groove 70, an actuating portion 71 and a through-hole 72.

As shown in FIGS. 21 and 22, the cam groove 70 engages the pivot pin 61a (See FIGS. 24A-24D) of the link member 6 to allow the movement of the pivot pin 61a. The cam groove 70 includes inclined groove portions 70a and 70b extending in a direction inclined with respect to the lancing and the retreating directions N1, N2, and a straight groove portion 70c extending in the lancing and the retreating directions N1, N2. The pivot pin 61a moves through the inclined groove portion 70a in moving the lancet holder 8 in the lancing direction N1 (See FIGS. 24B and 24C), whereas the pivot pin 61a moves through the inclined groove portion 70b in moving the lancet holder 8 in the retreating direction N2 (See FIGS. 24C and 24D). The pivot pin 61a moves through the straight groove portion 70c in moving the movable plate 7 in the retreating direction N2 without moving the lancet holder 8 in the lancing direction N1 or the retreating direction N2 (See FIGS. 24A and 24B). As better shown in FIG. 22, at the boundary between the inclined groove portion 70a and the straight groove portion 70c, the inclined groove portion 70a is made deeper than the straight groove portion 70c, whereby a stepped portion is provided between the groove portions 70a and 70c. Therefore, the pivot pin 61a cannot move from the inclined groove portion 70a to the straight groove portion 70c. On the other hand, at the boundary between the inclined groove portion 70b and the straight groove portion 70c, the straight groove portion 70c is made deeper than the inclined groove portion 70b, whereby a stepped portion is provided between the groove portions 70b and 70c. Therefore, the pivot pin 61a cannot move from the straight groove portion 70c to the inclined groove portion 70b. Therefore, the pivot pin 61a moves through the cam groove 70 in the clockwise direction in FIGS. 17 and 24A-24D.

As shown in FIGS. 20A and 20B, the actuating portion 71 is used to manually move the movable plate 7. The actuating portion 71 partially projects outward through an opening 20 of the housing 2 and is allowed to move through the opening 20 in the lancing and the retreating directions N1, N2.

The through-hole 72 is used to fix the movable plate 7, with the coil spring Sp storing the resilient force. Specifically, the fixation of the movable plate 7 is performed by engaging a hook 45a of a fixing member 45 with the through-hole 72. The fixing member 45 is biased, by a coil spring 46, toward the outside of the housing 2 at a press portion 45b rotatably supported by the housing 2. With such an arrangement, the hook 45a can engage the trough-hole 72 relatively strongly. When the press portion 45b is pressed toward the inner side of the housing 2, the hook 45a rotates toward the outside of the housing 2 and disengages from the thorough-hole 72.

Figure 23:
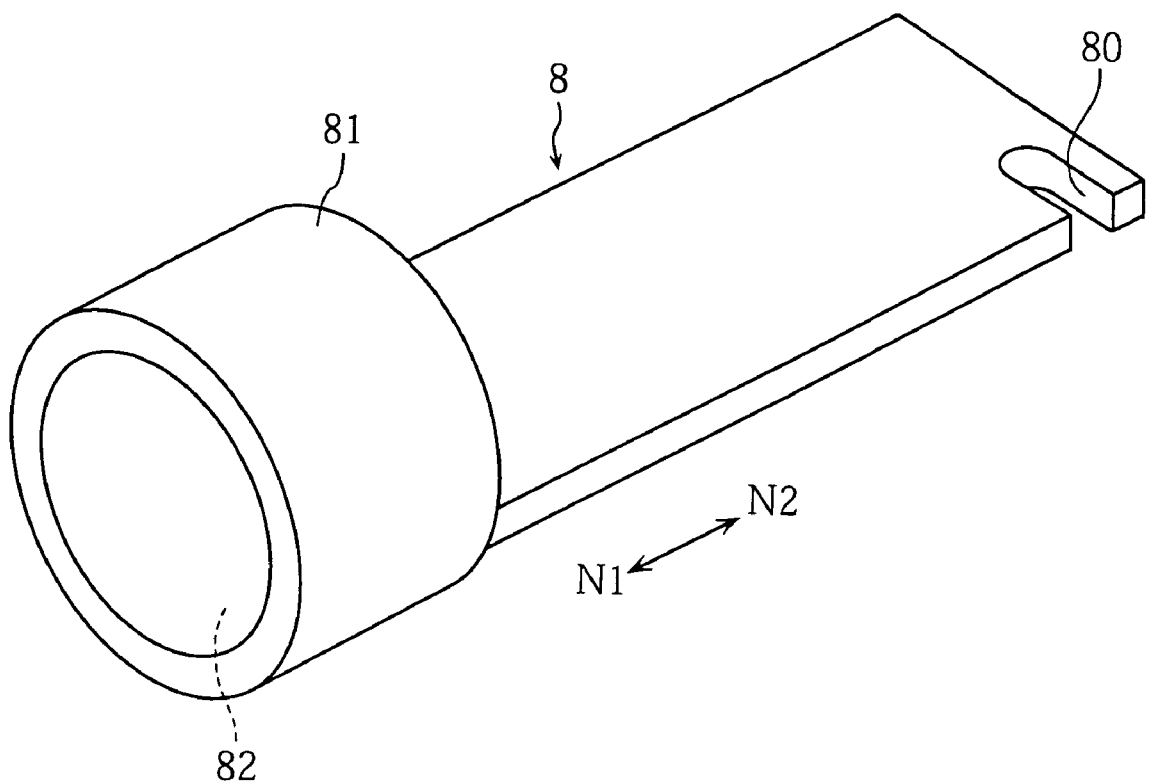
FIG. 23 is an entire perspective view of the lancet holder of the lancing apparatus shown in FIGS. 17 and 18.

As shown in FIG. 23, the lancet holder 8, which serves to hold and move the lancet 1 (See FIGS. 17 and 18), is movable in the lancing and the retreating directions N1 and N2, similarly to the movable plate 7 (See FIG. 22). The lancet holder 8 entirely extends in the lancing and the retreating directions N1 and N2, and includes a cutout 80 and a holder portion 81.

The cutout 80 serves to engage the pivot pin 62a and allow the movement of the pivot pin 62a (See FIGS. 24A-24B), and extends in a direction crossing the lancing and the retreating directions N1, N2. The holder portion 81 serves to hold the lancet 1 (See FIG. 1) and includes an accommodation space 82 for accommodating the lance 1.

The usage and operation principle of the lancing apparatus X2 will be described. It is to be noted that the following description is given on the assumption that, in the initial state, the movable plate 7 is positioned at the top dead center of the retreating direction N2, while the pivot pin 61a is positioned at the lower end of the straight groove portion 70c of the cam groove 70 of the movable plate 7, as shown in FIG. 24A.

First, to lance the skin by using the lancing apparatus X2, the lancet 1 is mounted to the holder portion 81 of the lancet holder 8 after the hook 45a of the fixing member 45 is engaged with the through-hole 72 of the movable plate 7, as shown in FIGS. 18 and 20. Alternatively, the hook 45a may be engaged with the through-hole 72 of the movable plate 7 after the lancet 1 is mounted to the portion 81.

As will be understood from FIGS. 20A and 20B, the engagement of the hook 45a with the through-hole 72 can be performed by moving the actuating portion 71 of the movable plate 7 a predetermined distance in the lancing direction N1. At this time, as shown in FIGS. 24A and 24B, since a stepped portion is provided between the inclined groove portion 70b and the straight groove portion 70c of the cam groove 70 (See FIG. 22), the pivot pin 61a of the link member 6 moves thorough the straight groove portion 70c of the cam groove 70. Therefore, the movable plate 7 moves in the lancing direction N1 without moving the lancet holder 8. When the movable plate 7 moves in the lancing direction N1, the coil spring Sp is expanded, so that the movable plate 7 is held in the housing 2 as biased in the retreating direction N2.

When the holding of the movable plate 7 and the mounting of the lancet 1 are completed, lancing of the skin can be performed by pressing the press portion 45b of the fixing member 45, as shown in FIGS. 20A and 20B. When the press portion 45b is pressed, the hook portion 45a rotates toward the outside of the housing 2 to disengage from the through-hole 72. Since the movable plate 7 is biased toward the retreating direction N2 as noted above, the movable plate 7 moves in the retreating direction N2 while compressing the coil spring Sp, as shown in FIGS. 24B-24D. During this movement, since a stepped portion is provided between the straight groove portion 70c and the inclined groove portion 70a (See FIG. 22), the pivot pin 61a of the link member 6 moves through the inclined groove portion 70a and then through the inclined groove portion 70b of the cam groove 70.

The link member 6 rotates around the rotation pin 63 clockwise in the figures to allow the pivot pin 61a to move through the inclined groove portion 70a and then rotates around the rotation pin 63 counterclockwise in the figures to allow the pivot pin 61a to move through the inclined groove portion 70b. In such pivotal movement of the pivot pin 61a, the pivot pin 62a also rotates clockwise and then counterclockwise. Therefore, in accordance with the pivotal movement of the pivot pin 62a, the lancet holder 8 moves in the lancing direction N1 to lance the skin and then moves in the retreating direction N2. In such reciprocal movement of the lancet holder 8, the lancing needle 11 of the lancet 1 lances the skin and then is pulled out from the skin.

In the lancing apparatus X2, the movable plate 7 can be easily fixed to the housing 2 by pushing down the actuating portion 71 of the movable plate 7. Further, the lancing of the skin can be performed just by pressing the press portion 45b of the fixing member 45. In this way, in the lancing apparatus X2, the lancing can be performed by extremely easy operations which can be performed with one hand, such as the pushing down of the actuating portion 71 and the pressing of the press portion 45b, so that the lancing apparatus is easy to use.

In the lancing apparatus X2, the coil spring Sp is expanded or compressed as the movable plate 7 moves. Therefore, unlike the case in which the coil spring Sp is twisted, exertion of a great load locally on an end of the spring, for example, can be avoided. Therefore, even when the coil spring Sp has a relatively low rigidity, the coil spring Sp can have a long life, which is advantageous in terms of the manufacturing cost.

Further, in the lancing apparatus X2, by releasing the movable plate 7 from the fixed state, the lancing needle 11 reciprocates between the wait position and the lancing position in accordance with the pivotal movement of the link member 6. Therefore, the same advantages as those of the foregoing lancing apparatus X1 (See FIG. 1, for example) can be provided. Firstly, in the lancing apparatus X2, the period of time during which the lancing needle 11 sticks in the skin can be shortened, so that the pain given to the patient can be reduced. Secondly, the lancing apparatus is safe because the lancing needle 11 is retreated after lancing, and the retreat of the lancing needle 11 after the lancing can be realized by a simple structure. Thirdly, the impact, impact noise and vibration in the lancing as well as the shaking of the lancing needle 11 can be suppressed, so that pain or discomfort given to the patient can be reduced.

Next, a third embodiment of the present invention will be described with reference to FIGS. 25A-25D. In these figures, the elements which are identical or similar to those of the foregoing lancing apparatuses X1 and X2 are designated by the same reference signs as those used for the foregoing lancing apparatuses.

The lancing apparatus X3 shown in FIGS. 25A-25D differs from the foregoing lancing apparatus X2 (See FIGS. 17 and 24A-24D) in configuration of the cam groove 70B of the movable plate 7B and structure to pull out the lancing needle 11 of the lancet 1 from the skin after sticking in the skin.

The cam groove 70B includes an inclined groove portion 70d for pivoting the link member 6. The link member 6 includes a pivot pin 61a which moves through the inclined groove portion 70d when the movable plate 7B moves in either of the lancing and the retreating directions N1 and N2.

The movable plate 7B is supported by a housing 2 via two coil springs Sp and Sp'. The coil spring Sp mainly serves to move the movable plate 7B in the lancing direction N1 by the stored resilient force. The coil spring Sp' mainly serves to store the resilient force when the movable plate 7B is moved in the lancing direction N1 and to move the movable plate 7B in the retreating direction N2 after the lancing needle 11 sticks in the skin. When no load is exerted from the outside on the movable plate 7B, the coil springs Sp and Sp' are in equilibrium, and the pivot pin 61a is positioned at the center of the inclined groove portion 70d.

As shown in FIGS. 25A and 25B, in the lancing apparatus X3, by moving the movable plate 7B in the lancing direction N1 and fixing to the housing 2, the coil spring Sp is expanded while the coil spring Sp' is compressed. In this state, the coil springs Sp and Sp' store the resilient force, and the pivot pin 61a is positioned at the upper end of the inclined groove portion 70d. As shown in FIGS. 25C and 25D, when the movable plate 7B is thereafter released from the state fixed to the housing 2, the movable plate 7B moves in the retreating direction N2, and the pivot pin 61a moves through the inclined groove portion 70d. By this movement, the entirety of the link member 6 rotates clockwise in the figures, whereby the lancet holder 8 and hence the lancet 1 move in the lancing direction N1. As shown in FIG. 25E, after the pivot pin 61a reaches the lower end of the inclined groove portion 70d and the lancing needle 11 sticks in the skin, a force toward the retreating direction N2 is exerted on the lancet holder 8 due to the resilient force of the coil spring Sp', so that the pivot pin 61a moves through the inclined groove portion 70d. As a result, the link member 6 rotates counterclockwise in the figures to move the lancet holder 8 and hence the lancet 1 in the retreating direction N2, whereby the lancing needle 11 is pulled out from the skin.

Next, a fourth embodiment of the present invention will be described with reference to FIGS. 26-30. In these figures, the elements which are identical or similar to those of the foregoing lancing apparatuses X1 and X2 are designated by the same reference signs as those used for the foregoing lancing apparatuses.

Figure 26:
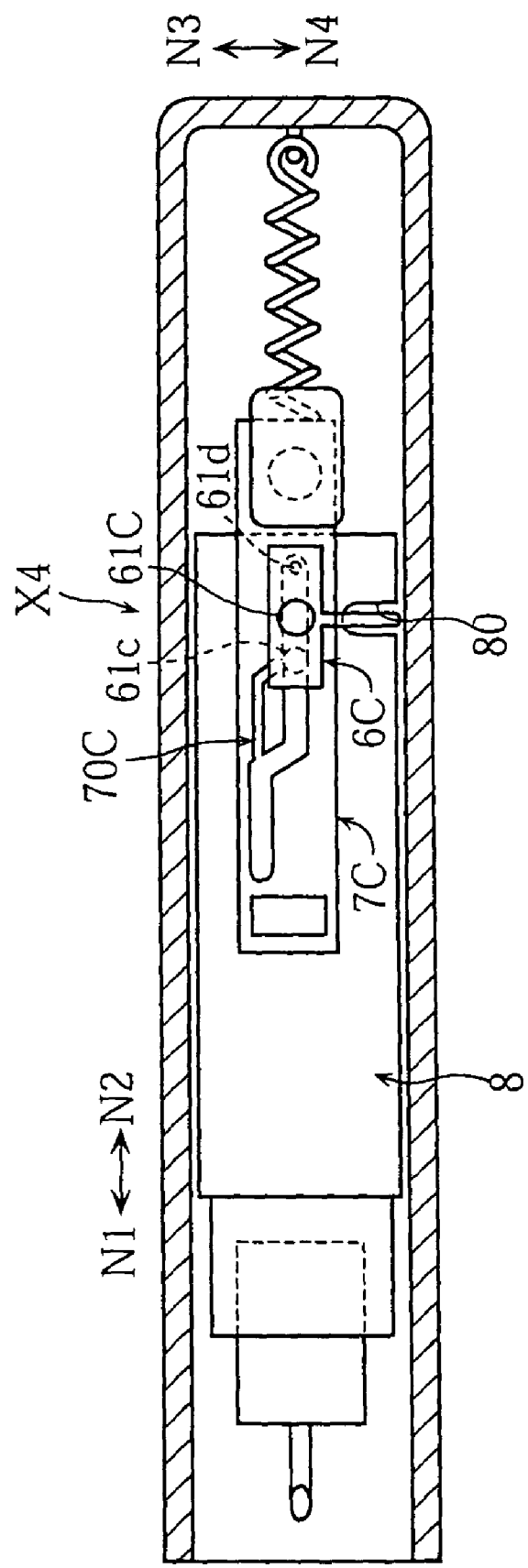
FIG. 26 is a sectional view of a lancing apparatus according to a fourth embodiment of the present invention.

The lancing apparatus X4 shown in FIG. 26 differs from the foregoing lancing apparatus X2 (See FIGS. 17 and 24A-24D) in structure of the link member 6C and the cam groove 70C of the movable plate 7C.

Figure 27:
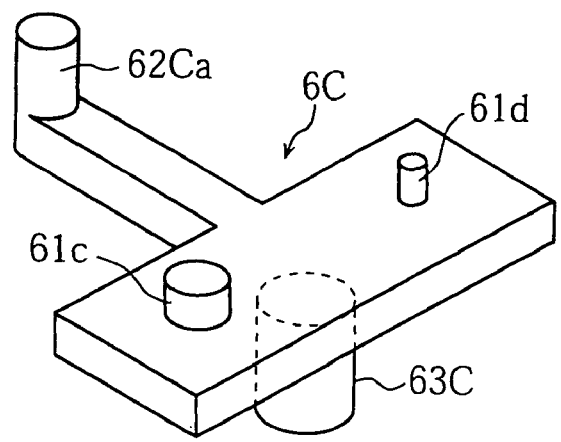
FIG. 27 is an entire perspective view of the link member of the lancing apparatus shown in FIG. 26.
Figure 28:
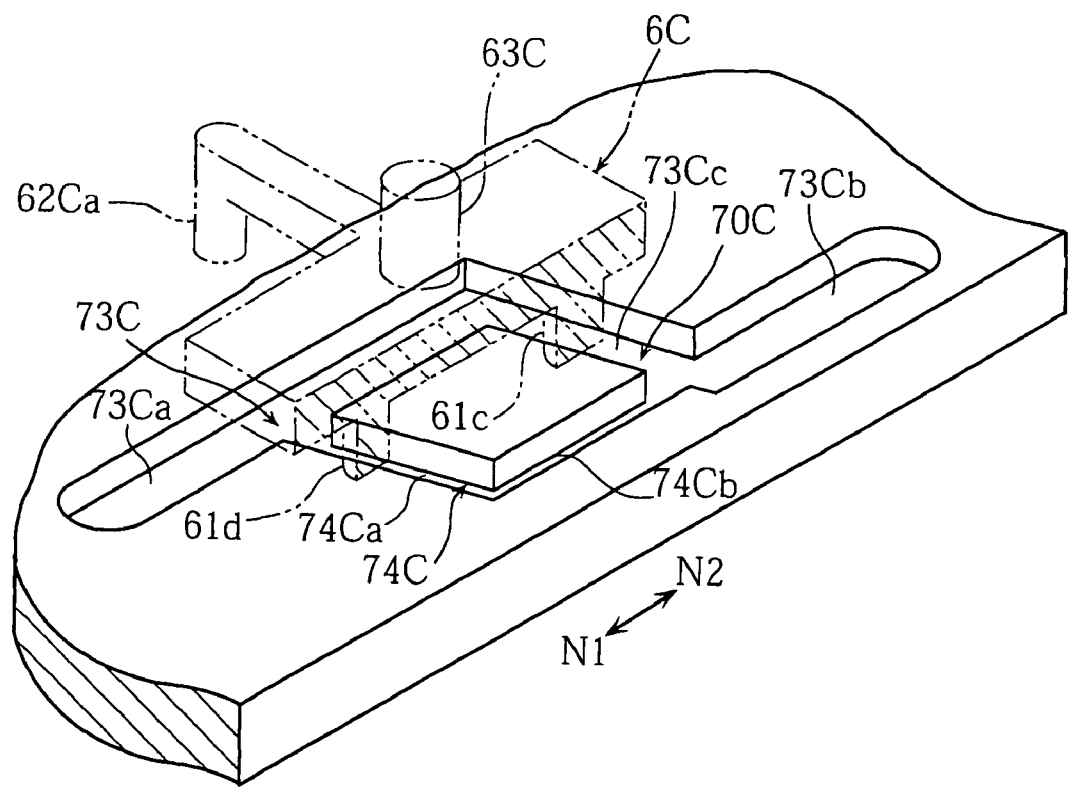
FIG. 28 is a perspective view showing the movable plate of the lancing apparatus of FIG. 26 as enlarged.

As shown in FIGS. 26-28, the link member 6C includes a large-diameter pivot pin 61c and a small-diameter pivot pin 61d for engagement with the cam groove 70C, and a pivot pin 62Ca for engagement with a cutout 80 of the lancet holder 8. The large-diameter pivot pin 61c is larger in diameter than the small-diameter pivot pin 61d. At about the midpoint between the large-diameter pivot pin 61c and the small-diameter pivot pin 61d is provided a rotation pin 63C. Though not clearly shown in the figures, the rotation pin 63C is supported by a housing 2 movably in directions N3 and N4 crossing the lancing and the retreating directions N1 and N2. For instance, the rotation pin 63C is made movable in the directions N3 and N4 by forming an elongated hole extending in the directions N3, N4 in the housing 2 and holding the rotation pin in the elongated hole.

As shown in FIGS. 26 and 28, the cam groove 70C includes a wide groove portion 73C and a narrow groove portion 74C. The wide groove portion 73C includes two straight portions 73Ca and 73Cb, and an inclined portion 73Cc connecting the two straight portions to each other. Respective lengths of the straight portions 73Ca, 73Cb and the inclined portion 73Cc are made equal or generally equal to the distance between the large-diameter pivot pin 61c and the small-diameter pivot pin 61d. The width of the wide groove portion 73C is made equal to or larger than the diameter of the large-diameter pivot pin 61c. The narrow groove portion 74C includes an inclined portion 74Ca and a straight portion 74Cb connected to each other. The inclined portion 74Ca extends parallel to the inclined portion 73Cc of the wide groove portion 73C. The distance between the inclined portion 73Cc and the inclined portion 74Ca is generally equal to the distance between the large-diameter pivot pin 61c and the small-diameter pivot pin 61d in the lancing and the retreating directions N1 and N2. The inclined portion 73Cc has an end connected to the straight portion 73Ca of the wide groove portion 73C. The straight portion 74Cb has an end connected to the wide groove portion 73C at the boundary between the straight portion 73Cb and the inclined portion 73Cc of the wide groove portion 73C. Respective lengths of the inclined portion 74Ca and the straight portion 74Cb are made equal or generally equal to the distance between the large-diameter pivot portion 61c and the small-diameter pivot portion 61d. The width of the narrow groove portion 74C is made equal to or larger than the diameter of the small-diameter pivot pin 61d and smaller than the diameter of the large-diameter pivot pin 61c.

As shown in FIG. 29A, in the lancing apparatus X4, when no external load is exerted on the movable plate 7C, both of the large-diameter pivot pin 61c and the small-diameter pivot pin 61d are positioned in the straight portion 73Cb of the wide groove portion 73C. As shown in FIGS. 29A and 29B, by moving the movable plate 7C in the lancing direction N1, the movable plate can be fixed to the housing 2, with the spring Sp storing the resilient force. When the movable plate 7C is moved in the lancing direction N1, the large-diameter pivot pin 61c moves through the straight portion 73Cb of the wide groove 73, and the small-diameter pivot pin 61d moves through the straight portion 74Cb of the narrow groove portion 74C. Subsequently, as shown in FIG. 29C, the small-diameter pivot pin 61d moves through the inclined portion 74Ca of the narrow groove portion 74C. However, the large-diameter pivot pin 61c cannot move through the narrow groove portion 74C because of its diameter which is larger than the width of the narrow groove portion 74C, and hence, moves through the inclined portion 73Cc of the wide groove portion 73C. In this way, the large-diameter pivot pin 61c and the small-diameter pivot pin 61d move through the inclined portions 73Cc and 74Ca to translate the entirety of the link member 6 in the N4 direction in the figure while keeping aligned in the lancing and the retreating directions N1 and N2. Thereafter, as shown in FIGS. 29D and 29E, both of the large-diameter pivot pin 61c and the small-diameter pivot pin 61d move through the straight portion 73Ca of the wide groove portion 73C.

As will be understood from FIGS. 29A-29E, when the movable plate 7C is moved in the lancing direction N1, the large-diameter pivot pin 61c and the small-diameter pivot pin 61d of the link member 6 keep aligned in the lancing and the retreating directions N1 and N2, and the link member 6 moves relative to the movable plate 7C without rotating. Therefore, when the movable plate 7C is moved in the lancing direction N1 for fixation to the housing 2, the lancet holder 8 does not move in the lancing direction N1 or the retreating direction N2. Therefore, even when the movable plate 7C is moved for fixation to the housing 2 with the lancet 1 mounted to the lancet holder 8, the lancing needle 11 of the lancet 1 does not project from the housing 2.

As shown in FIGS. 30A-30F, when the movable plate 7C is released from the fixed state, the movable plate 7C moves in the retreating direction N2. At this time, both of the large-diameter pivot pin 61*c* and the small-diameter pivot pin 61*d* move through the wide groove portion 73C. Specifically, the large-diameter pin 61*c* moves through the straight portion 73Ca, the inclined portion 73Cc and the straight portion 73Cb, whereas the small-diameter pivot pin 61*d* moves through the straight portion 73*ca* and the inclined portion 73Cc. In this way, both of the large-diameter pivot portion 61*c* and the small-diameter pivot portion 61*d* pass through the inclined portion 73Cc.

Figure 30A:
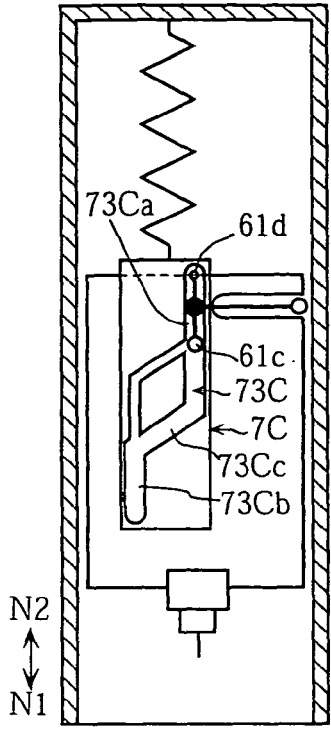
FIGS. 30A-30F are schematic sectional views for describing the lancing operation of the lancing apparatus shown in FIG. 26.
Figure 30B:
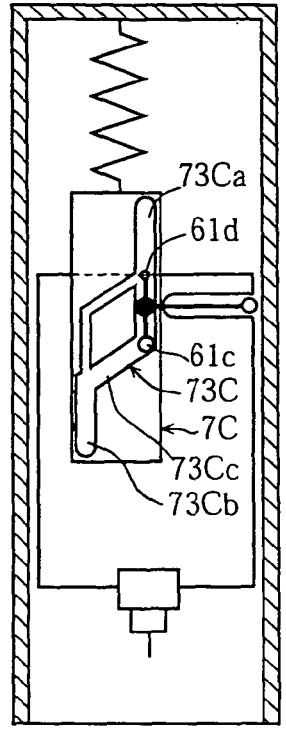
Figure 30C:
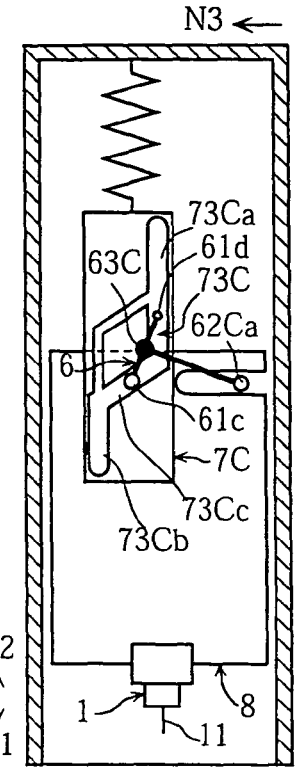
Figure 30D:
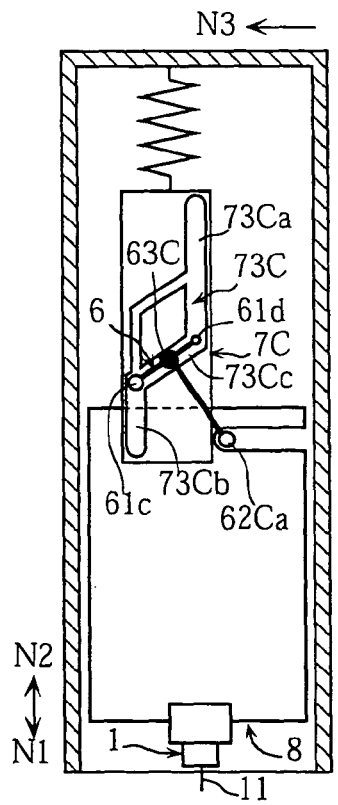

As shown in FIGS. 30C and 30D, when the large-diameter pivot pin 61*c* moves through the inclined portion 73Cc, the small-diameter pivot pin 61*d* moves through the straight portion 73Ca, so that the entirety of the link member 6 rotates clockwise in the figures, while the rotation pin 63C moves in the N3 direction. At this time, the pivot pin 62Ca also rotates clockwise to move the lancet holder 8 and hence the lancet 1 in the lancing direction N1, so that the lancing needle 11 of the lancet 1 sticks in the skin.

Figure 30E:
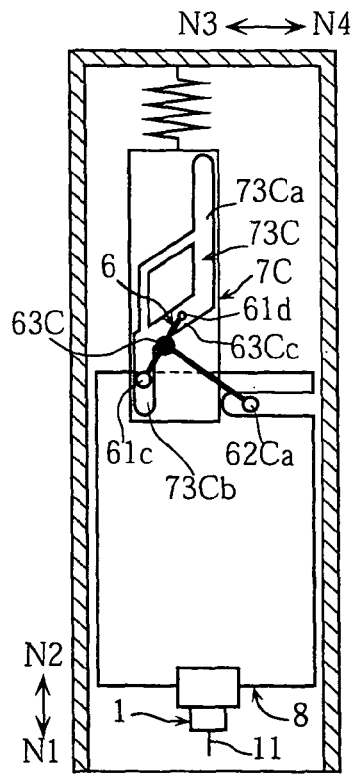
Figure 30F:
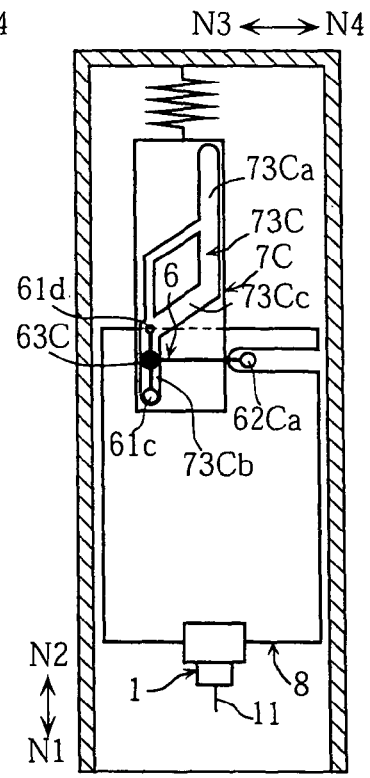

On the other hand, as shown in FIGS. 30E and 30F, when the small-diameter pivot pin 60*d* moves through the inclined portion 73Cc, the large-diameter pivot pin 61*c* moves through the straight portion 73Cb. Therefore, the entirety of the link member 6 rotates counterclockwise in the figures, while the rotation pin 63C moves in the N4 direction. At this time, the pivot pin 62Ca also rotates counterclockwise to move the lancet holder 8 and hence the lancet 1 in the retreating direction N2, so that the lancing needle 11 is pulled out from the skin.

The lancing operation similar to that of the lancing apparatus X4 can be performed by a cam groove and a link member designed as follows. As to the cam groove, two groove portions corresponding to the wide groove portion 73C and the narrow grove portion 74C of the cam groove 70C of the lancing apparatus X4 are provided to be equal in width and different in depth from each other. As to the link member, two pins corresponding to the large-diameter pivot pin 61*c* and the small-diameter pivot pin 61*d* of the link member 6 of the lancing apparatus X4 are provided to be equal in diameter and different in length from each other.

Next, a fifth embodiment of the present invention will be described with reference to FIGS. 31A-31D and 32A-32D. In these figures, the elements which are identical or similar to those of the foregoing lancing apparatuses X1 and X2 are designated by the same reference signs as those used for the foregoing lancing apparatuses.

Figure 31A:
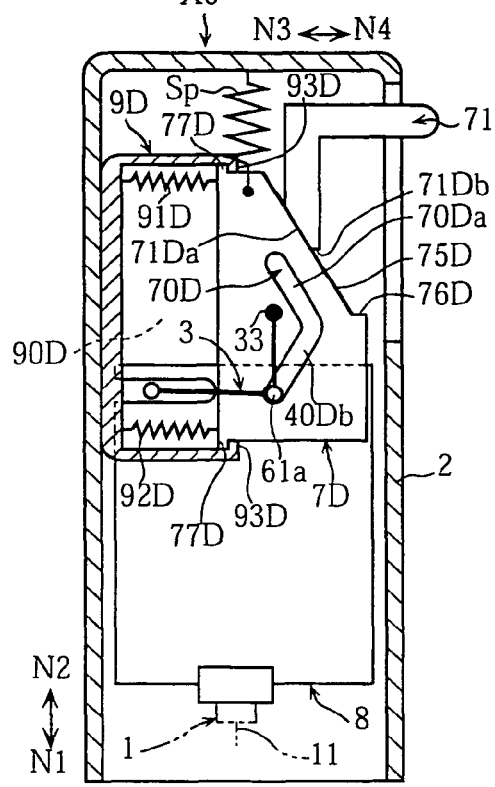
FIGS. 31A-31D are schematic sectional views showing a lancing apparatus according to a fifth embodiment of the present invention and the operation thereof.

As shown in FIG. 31A, the lancing apparatus X5 differs from the foregoing lancing apparatus X2 (See FIGS. 17 and 24A-24D) in structure of the cam groove 70D of the movable plate 7D and operation of the link member 6 and the movable plate 7D.

The cam groove 70D has a configuration provided by omitting the straight groove portion 70*c* (See FIG. 22) from the cam groove 70 of the lancing apparatus X2. Specifically, the cam groove of this embodiment is made up of two inclined groove portions 70Da and 70Db connected to each other. The inclined groove portions 70Da and 70Db have a constant depth.

The link member 6 is movable in the directions N3 and N4 extending perpendicularly to the lancing and the retreating directions N1 and N2 and is rotatable around the rotation pin 63. Though not shown in the figure, the link member 6 is made movable in the directions N3 and N4 by forming an elongated hole extending in the directions N3 and N4 in the housing 2 and holding the rotation pin 63 in the elongated hole, for example.

The movable plate 7D includes an inclined surface 75D and a stopper surface 76D and is movable in the lancing and the retreating direction N1, N2 and in the arrows N3, N4 directions. The movable plate 7D is movable in the lancing and the retreating directions N1, N2 together with a biasing guide 9D and an actuating member 71D and also movable in the arrows N3, N4 directions independently from the biasing guide 9D and the actuating member 71D.

The biasing guide 9D includes a space 90D for allowing the movement of the movable plate 7D in the arrows N3, N4 directions. A pair of coil springs 91D and 92D arranged in the space 90D connect the biasing guide 9D and the movable plate 7D to each other. The movable plate 7D and the biasing guide 9D are respectively provided with stoppers 77D and 93D for restricting the movement of the movable plate 7D in the arrow N4 direction. When no external load is exerted on the movable plate 7D, the movable plate 7D is biased in the arrow N4 direction by the coil springs 91D and 92D, with the movement thereof in the arrow N4 direction prevented by the stoppers 77D and 93D.

The actuating member 71D is movable only in the lancing and the retreating directions N1 and N2. Such a manner of movement of the actuating member 71D is realized by providing the housing 2 with a guide for preventing the movement of the actuating member 71D in the arrows N3, N4 directions. The actuating member 71D includes an inclined surface 71Da and a stopper surface 71Db. The inclined surface 71Da is brought into contact with the inclined surface 75D of the movable plate 7D when the movable plate 7D moves in the arrow N3 direction. The stopper surface 71Db is brought into contact with the stopper surface 76D of the movable plate 7D when the movable plate 7D moves in the lancing direction N1 or in the retreating direction N2.

Figure 31B:
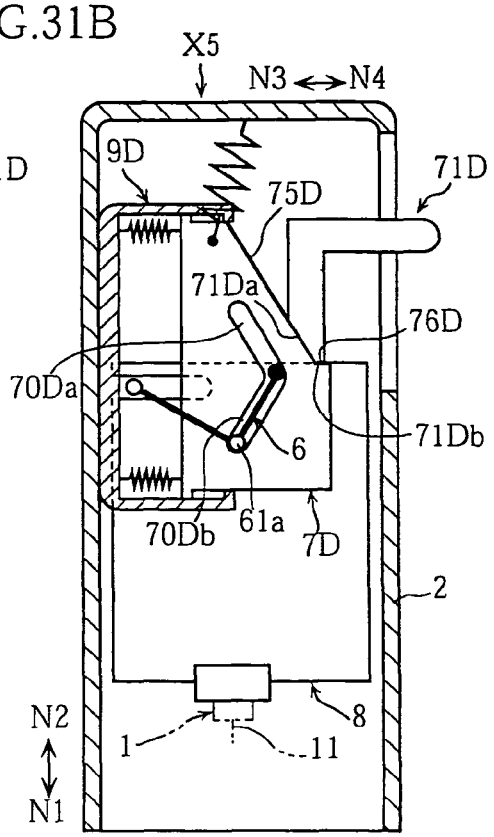
Figure 31C:
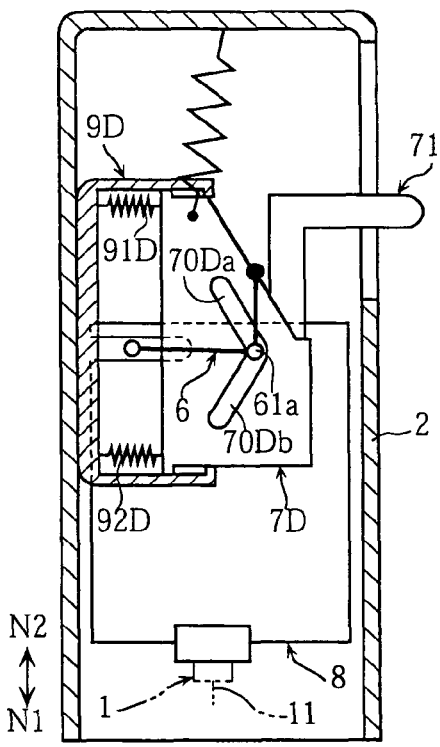
Figure 31D:
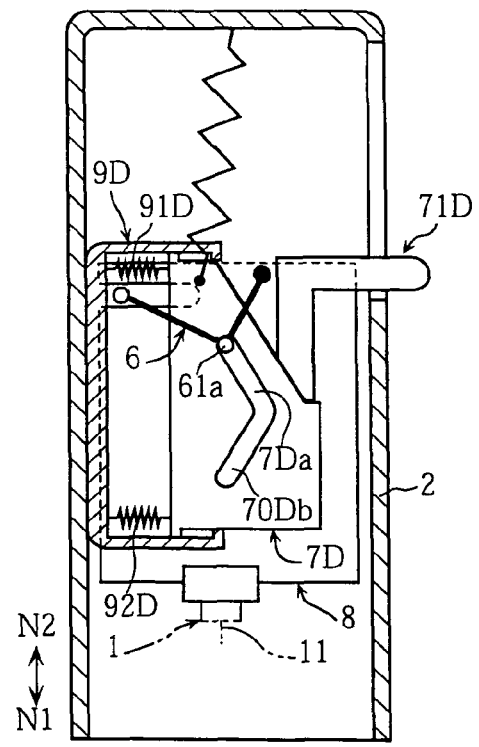

As noted before, in the lancing apparatus X5, when no external load is exerted on the movable plate 7D, the coil springs 91D and 92D are in the expanded state, and the movable plate 7D is biased in the N4 direction. As shown in FIGS. 31A-31D, in performing the lancing operation, the movable plate 7D, along with the biasing guide 9D, is moved in the lancing direction N1 by moving the actuating member 71D in the lancing direction N1. As shown in FIGS. 31A and 31B, since the movement of the actuating member 71D in the arrows N3, N4 directions is prevented, the inclined surface 71Da of the actuating member 71D slides on the inclined surface 75D of the movable plate 7D until the stopper surface 71Db of the actuating member 71D engages the stopper surface 76D of the movable plate 71D, whereby the movable plate 7D is moved in the arrow N3 direction. In accordance with this operation, the link member 6 rotates clockwise in the figures, and the lancet holder 8 is lifted in the retreating direction N2. As shown in FIGS. 31B-31D, when the stopper surface 71Db of the actuating member 71D engages the stopper surface 76D of the movable plate 7D, the movable plate 7D, along with the actuating member 71D, moves in the lancing direction N1. At this time, the pivot pin 61*a* moves through the inclined groove portions 70Da and 70Db. During when the pivot pin 61*a* moves through the inclined groove portion 70Db, the link member 6 rotates counterclockwise in the figures to move the lancet holder 8 in the lancing direction N1. During when the pivot pin 61*a* moves through the inclined groove portion 70Da, the link member 6 rotates clockwise in the figures to move the lancet holder 8 in the retreating direction N2. When the movable plate 7D is moved more than a predetermined distance, the movable plate is fixed to the housing 2 as biased in the retreating direction N2 and the arrow N4 direction, with the coil springs Sp, 91D and 92D storing the resilient force.

In the above operation for fixing the movable plate 7D, the lancet holder 8 moves in the lancing direction N1 when the pivot pin 61*a* moves through the inclined groove portion 70Db. However, since the lancet holder 8 is lifted in advance in the retreating direction N2 by moving the movable plate 7D in the arrow N3 direction, the lancing needle 11 of the lancet 1 is prevented from projecting from the housing 2 even when the lancet 11 is mounted to the lancet holder 8 in advance.

Figure 32A:
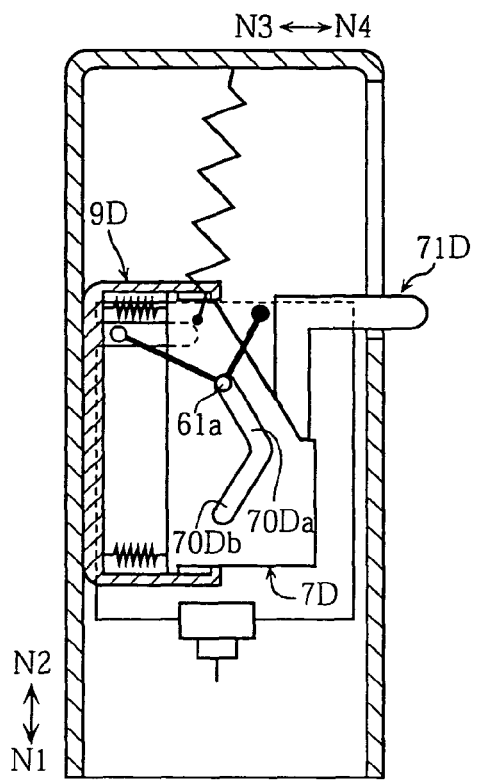
FIGS. 32A-32D are schematic sectional views for describing the lancing operation of the lancing apparatus according to the fifth embodiment of the present invention.
Figure 32B:
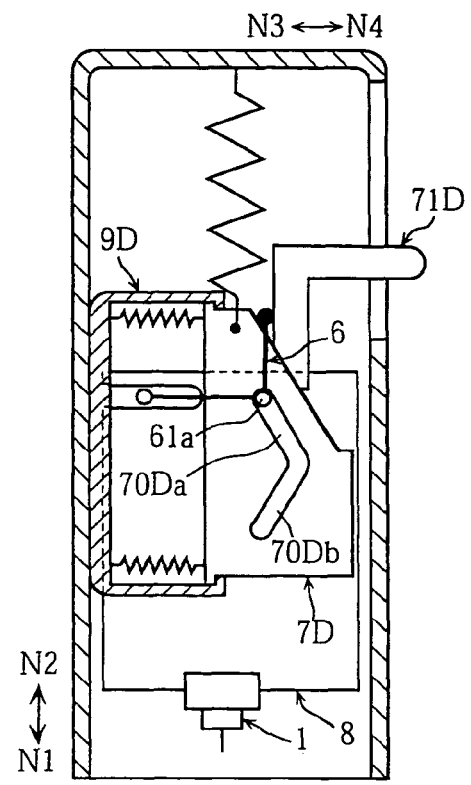

As shown in FIGS. 32A-32D, when the movable plate 7D is released from the fixed state, the movable plate 7D moves in the retreating direction N2. As shown in FIGS. 32A and 32B, since the external force exerting on the actuating member 71D has been removed, the movable plate 7D moves in the arrow N4 direction independently from the biasing guide 9D due to the biasing force exerted on the movable plate 7D in the N4 direction. Since the biasing force toward the retreating direction N2 is exerted on the movable plate 7D, the movable plate 7D moves in the retreating direction N2 along with the biasing guide 9D. During this movement, the pivot pin 61*a* moves through the inclined groove portions 70Da and 70Db.

Figure 32C:
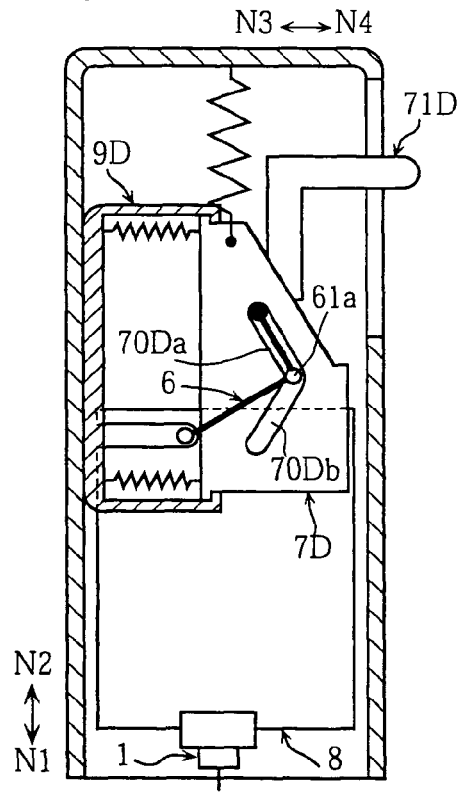
Figure 32D:
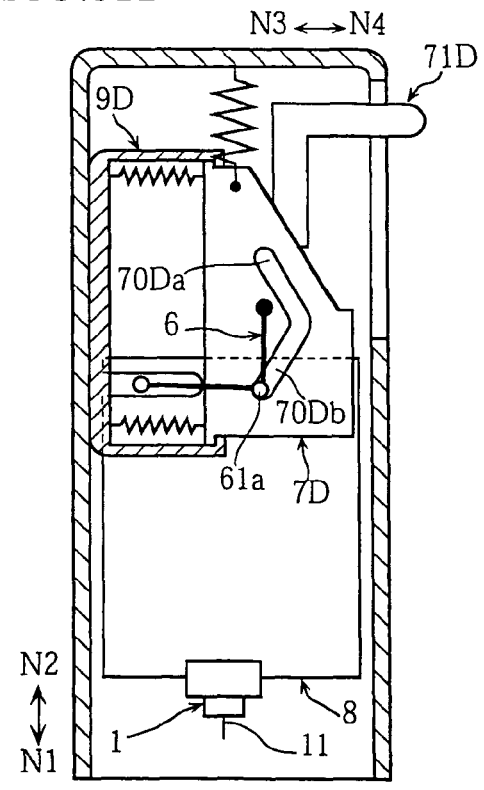
Figure 33A:
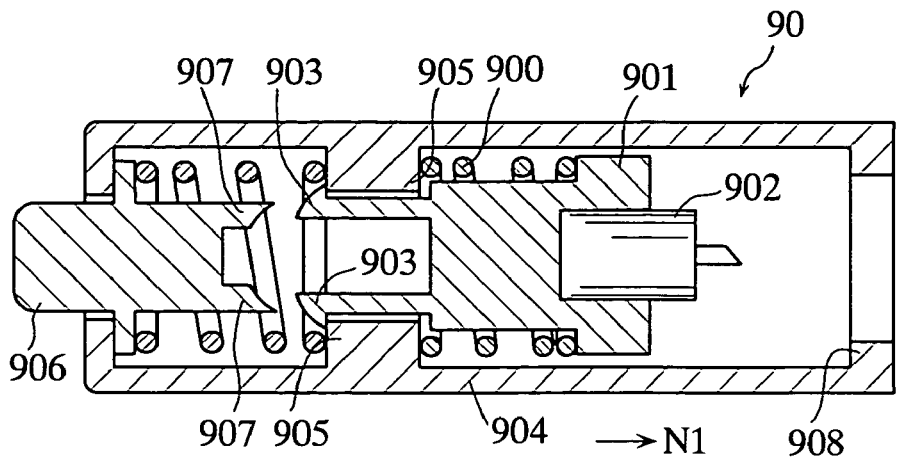
FIGS. 33A-33C are sectional views showing an example of prior art lancing apparatus.
Figure 33B:
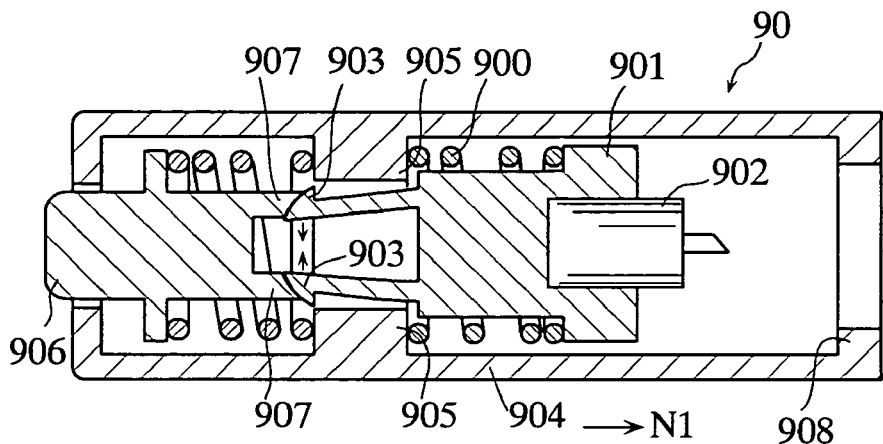
Figure 33C:
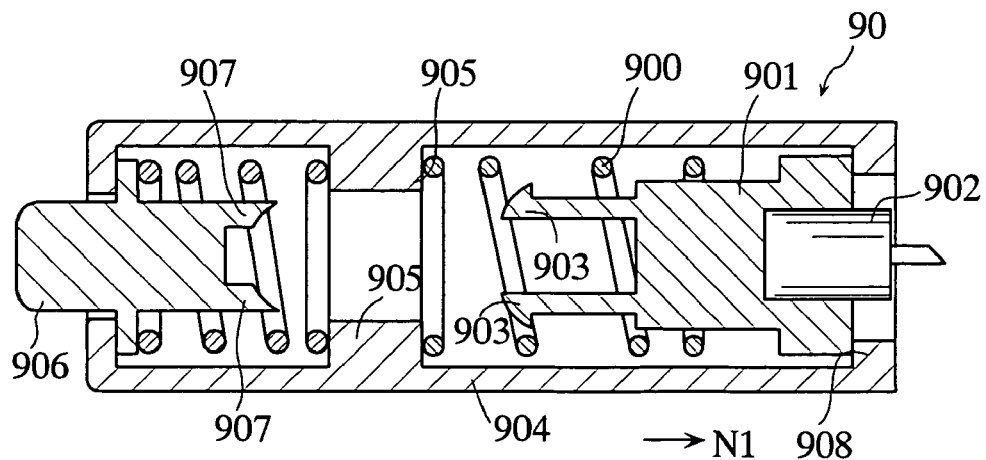

During when the pivot pin 61*a* moves through the inclined groove portion 70Da as shown in FIGS. 32B and 32C, the link member 6 rotates counterclockwise in the figures to move the movable plate 7D in the lancing direction N1. Therefore, the lancet holder 8 and hence the lancet 1 move in the lancing direction N1, so that the lancing needle 11 of the lancet 1 lances the skin. During when the pivot pin 61*a* moves through the inclined groove portion 70Db as shown in FIGS. 32C and 32D, the link member 6 rotates clockwise in the figures to move the movable plate 7D in the retreating direction N2. Therefore, the lancet holder 8 and hence the lancet 1 move in the retreating direction N2, so that the lancing needle 11 of the lancet 1 is pulled out from the skin.

The biasing guide 9D moves in the lancing direction N1 or the retreating direction N2 in contact with the inner surface of the housing 2, and it is preferable that the structure between the biasing guide 9D and the housing 2 is so designed as to reduce the dynamic friction. For instance, the inner surface of the housing 2 or the outer surface of the biasing guide 9D is made smooth or formed with a plurality of slits or recesses for reducing the contact area.

The present invention is not limited to the foregoing first through the fifth embodiments and may be modified in various ways. For example, in each of the lancing apparatuses X1-X5, the movable plate 31, 7A-7D is moved by the resilient force of a coil spring Sp. However, a resilient member other than the coil spring Sp may be used to exert a driving force on the movable plate 31, 7A-7D. Alternatively, the movable plate 31, 7A-7D may be moved by utilizing a driving force such as a force of air or an electromagnetic force.

Although the lancing needle 11 is removably attached to the lancet holder 32, 8 as a mode of the lancet holder 1, the lancing needle 11 may be integrally formed on a movable member which operates similarly to the lancet holder 32, 8.

The invention claimed is:

1. A lancing apparatus for moving a lancing element in a lancing direction from a wait position to a lancing position to lance an intended portion with the lancing element, the lancing apparatus comprising:
    a first member which is reciprocally movable in the lancing direction and in a retreating direction which is opposite from the lancing direction;
    a second member which moves along with the lancing element and performs reciprocal movement in the lancing direction and the retreating direction in accordance with the movement of the first member; and
    movement conversion means for converting the reciprocal movement of the first member into the reciprocal movement of the second member in a manner such that a directional change of movement of the second member from the lancing direction to the retreating direction is performed during a one-way stroke of the first member in one of the lancing direction and the retreating direction;
    wherein the first member is reciprocally movable between a first fixed position and a second fixed position;
    wherein the second member performs one cycle of reciprocal movement between a third fixed position and a fourth fixed position during one cycle of reciprocal movement of the first member between the first fixed position and the second fixed position.

2. The lancing apparatus according to claim 1, wherein the second member performs turning-back movement while the first member moves straight between the first fixed position and the second fixed position.

3. The lancing apparatus according to claim 2, wherein the lancing element is positioned at the lancing position when the second member is positioned at the third fixed position, and the lancing element is positioned at the wait position when the second member is positioned at an intermediate region between the third fixed position and the fourth fixed position.

4. The lancing apparatus according to claim 1, wherein the lancing element moves from the wait position to the lancing position when the first member moves in the retreating direction.

5. The lancing apparatus according to claim 1, wherein when the first member performs one cycle of reciprocal movement, the second member performs one cycle of reciprocal movement which is phase-shifted substantially by 90 degrees from the first member.

6. The lancing apparatus according to claim 1, the movement conversion means comprises a third member for connecting the first member and the second member to each other and converting movement of the first member into reciprocal movement of the second member.

7. The lancing apparatus according to claim 6, wherein the third member includes a rotation shaft whose position is fixed, a first movable portion which engages the first member and is rotatable around the rotation shaft, and a second movable portion which engages the second member and is rotatable around the rotation shaft.

8. The lancing apparatus according to claim 7, wherein the first member includes a first engagement portion for allowing the rotation of the first movable portion; and
    wherein the second member includes a second engagement portion for allowing the rotation of the second movable portion.

9. The lancing apparatus according to claim 8, wherein at least one of the first and the second engagement portions includes an inclined portion which is inclined with respect to a transverse direction extending perpendicularly to the lancing and the retreating directions.

10. The lancing apparatus according to claim 9, wherein the inclined portion has opposite ends each of which is connected to a straight portion extending in the transverse direction.

11. The lancing apparatus according to claim 10, wherein, of the first and the second movable portions, the movable portion which engages the inclined portion moves through the inclined portion when the lancing element moves from the wait position to the lancing position and moves through the straight portion when the lancing element moves from the lancing position in the retreating direction.

12. The lancing apparatus according to claim 9, wherein the inclined portion is provided in one of the first and the second engagement portions, whereas the other of the first and the second engagement portions extends substantially in the transverse direction.

13. The lancing apparatus according to claim 1, wherein the first member is fixed while being biased when the lancing element is positioned at the wait position, and the first member is moved by the biasing force when released from the fixed state.

14. The lancing apparatus according to claim 6, wherein the third member is pivotable to convert the movement of the first member into the reciprocal movement of the second member by the pivotal movement.

15. The lancing apparatus according to claim 14, wherein the third member includes a pivot shaft, a first movable portion which engages the first member and is pivotable around the pivot shaft, and a second movable portion which engages the second member and is pivotable around the pivot shaft.

16. The lancing apparatus according to claim 15, wherein the first member includes an engagement portion for engaging the first movable portion and controlling movement of the third member in accordance with a position where the first movable portion engages.

17. The lancing apparatus according to claim 16, wherein the engagement portion includes an inclined portion for pivoting the third member to move the second member in the lancing direction.

18. The lancing apparatus according to claim 17, wherein the engagement portion includes an additional inclined portion for pivoting the third member to move the second member in the retreating direction.

19. The lancing apparatus according to claim 16, wherein the engagement portion includes a straight portion extending in the lancing and the retreating directions for moving the first member in the lancing direction or the retreating direction without moving the second and the third members in the lancing and the retreating directions.

20. The lancing apparatus according to claim 17, further comprising a resilient member for moving the second member in the retreating direction after the intended portion is lanced with the lancing element.

21. The lancing apparatus according to claim 16, wherein the first movable portion includes a first and a second pins; and
wherein the engagement portion includes an inclined portion with which the first pin engages in moving the second member in the lancing direction and with which the second pin engages in moving the second member in the retreating direction.

22. The lancing apparatus according to claim 21, wherein the first member includes an additional engagement portion with which the second pin selectively engages when the first member moves in the retreating direction.

23. The lancing apparatus according to claim 22, wherein the first pin is larger in diameter than the second pin, and;
wherein the additional engagement portion has a width which is smaller than diameters of the engagement portion and the first pin.

24. The lancing apparatus according to claim 14, wherein the first member is movable in a crossing direction crossing the lancing and the retreating directions to pivot the third member to move the second member in the retreating direction.

25. The lancing apparatus according to claim 24, further comprising an actuating member for moving the first member;
wherein each of the first member and the actuating member includes an inclined surface, and the first member moves in the crossing direction by moving the inclined surface of the actuating member along the inclined surface of the first member.

26. The lancing apparatus according to claim 25, further comprising a guide which moves along with the first member in the lancing direction or the retreating direction, and a resilient member for connecting the guide and the first member to each other and biasing the first member in the crossing direction crossing the lancing and the retreating directions.

27. A lancing apparatus for moving a lancing element in a lancing direction from a wait position to a lancing position to lance an intended portion with the lancing element, the lancing apparatus comprising:
a housing;
a first member which is reciprocally movable within the housing in the lancing direction and in a retreating direction which is opposite from the lancing direction;
a second member which moves within the housing along with the lancing element and performs reciprocal movement in the lancing direction and the retreating direction in accordance with the movement of the first member; and
a movement conversion mechanism for converting the reciprocal movement of the first member into the reciprocal movement of the second member, the movement conversion mechanism including a stationary pin held at a fixed position relative to the housing, a first link arm connected to the first member and to the stationary pin for pivoting about the stationary pin, and a second link arm connected to the first link arm and to the second member for pivoting about the stationary pin, an angle being formed between the first and second link arms in a pivoting direction of the first and second link arms about the stationary pin.

28. A lancing apparatus for moving a lancing element in a lancing direction from a wait position to a lancing position to lance an intended portion with the lancing element, the lancing apparatus comprising:
a housing;
a first member, which is reciprocally movable within the housing in the lancing direction and in a retreating direction, which is opposite from the lancing direction;
a second member, which moves within the housing along with the lancing element and performs reciprocal movement in the lancing direction and the retreating direction in accordance with the movement of the first member; and
a movement conversion mechanism for converting the reciprocal movement of the first member into the reciprocal movement of the second member, the movement conversion mechanism including a stationary pin held at a fixed position relative to the housing, and a link member supported on the stationary pin for pivoting about the stationary pin,
wherein the link member includes a first arm carrying a first movable pin connected to the first member, and a second arm carrying a second movable pin connected to the second member, the first arm being connected to the second arm at an angle that is defined as an angle between the first and second arms in a pivoting direction of the link member about the stationary pin, said angle being invariable regardless of positions of the first and second members.

* * * * *